United States Patent
Maisano et al.

(10) Patent No.: US 10,206,673 B2
(45) Date of Patent: Feb. 19, 2019

(54) SUTURE-SECURING FOR CARDIAC VALVE REPAIR

(71) Applicant: 4TECH INC., Waltham, MA (US)

(72) Inventors: Francesco Maisano, Zürich (CH); Hugo Vanermen, Knocke-le-Zoute (BE); Ottavio Alfieri, Brescia (IT); Idan Tobis, Beth Hashmonai (IL); Andrea Guidotti, Zürich (CH); Paolo Denti, Opera (IT)

(73) Assignee: 4TECH, INC., Waltham, MA (US)

( * ) Notice: Subject to any disclaimer, the term of this patent is extended or adjusted under 35 U.S.C. 154(b) by 171 days.

(21) Appl. No.: 15/267,769

(22) Filed: Sep. 16, 2016

(65) Prior Publication Data

US 2017/0000474 A1  Jan. 5, 2017

Related U.S. Application Data

(60) Continuation of application No. 14/548,286, filed on Dec. 29, 2014, which is a division of application No.
(Continued)

(51) Int. Cl.
*A61B 17/04* (2006.01)
*A61F 2/24* (2006.01)
(Continued)

(52) U.S. Cl.
CPC .... *A61B 17/0487* (2013.01); *A61B 17/00234* (2013.01); *A61B 17/0401* (2013.01);
(Continued)

(58) Field of Classification Search
CPC ... A61B 17/0487; A61B 17/08; A61B 17/122; A61B 2017/1225; A61B 17/32;
(Continued)

(56) References Cited

U.S. PATENT DOCUMENTS 4,200,107 A * 4/1980 Reid .................. A61F 6/206
 128/843
4,214,349 A  7/1980 Munch
(Continued)

FOREIGN PATENT DOCUMENTS

DE  102007043830 A1  4/2009
EP  1568326 A1  8/2005
(Continued)

OTHER PUBLICATIONS

Shikhar Agarwal, et al; "Interventional Cardiology Perspective of Functional Tricuspid Regurgitation", Circulation Cardiovascular Interventions, vol. 2, Issue 6, pp. 565-573, Dec. 2009.
(Continued)

*Primary Examiner* — Christopher L Templeton
(74) *Attorney, Agent, or Firm* — UltimatEdge IP Law Group, P.C.; Dean G. Stathakis; Vito A. Canuso, III

(57) ABSTRACT

Apparatus is provided that includes a casing, shaped to define a cavity, and one or more openings in the casing, in which openings one or more sutures are disposable; and a core, disposed in the cavity, and shaped to define a lumen in which the sutures are disposable. The apparatus has an unlocked configuration in which the sutures are disposable within and slidable through the openings and the lumen, and a locking configuration in which the sutures are inhibited from sliding through the openings and the lumen. The apparatus is movable from the unlocked configuration to the locking configuration, and is configured such that, when the sutures are disposed within the openings and the lumen, and the apparatus moves from the unlocked configuration to the locking configuration, the apparatus cuts the sutures at a cutting site, and becomes coupled to the sutures at a coupling site.

6 Claims, 17 Drawing Sheets

Related U.S. Application Data

13/485,145, filed on May 31, 2012, now Pat. No. 8,961,594.

(51) Int. Cl.
*A61B 17/064* (2006.01)
*A61B 17/00* (2006.01)

(52) U.S. Cl.
CPC .......... *A61B 17/064* (2013.01); *A61F 2/2436* (2013.01); *A61F 2/2445* (2013.01); *A61F 2/2487* (2013.01); *A61B 2017/00243* (2013.01); *A61B 2017/00783* (2013.01); *A61B 2017/0414* (2013.01); *A61B 2017/0441* (2013.01); *A61B 2017/0464* (2013.01); *A61B 2017/0641* (2013.01); *A61F 2220/0016* (2013.01); *A61F 2220/0075* (2013.01); *A61F 2230/0006* (2013.01)

(58) Field of Classification Search
CPC ........... A61B 2017/0496; F16G 11/101; Y10T 24/3984; A61F 6/206; A61F 6/20; A61M 2039/282
See application file for complete search history.

(56) References Cited

U.S. PATENT DOCUMENTS

| | | | |
|---|---|---|---|
| 4,288,891 A * | 9/1981 | Boden | F16G 11/101 24/115 G |
| 4,405,313 A | 9/1983 | Sisley et al. | |
| 4,423,525 A | 1/1984 | Vallana et al. | |
| 4,444,207 A | 4/1984 | Robicsek | |
| 4,493,329 A | 1/1985 | Crawford et al. | |
| 4,532,926 A | 8/1985 | O'Holla | |
| 4,548,202 A | 10/1985 | Duncan | |
| 4,625,727 A | 12/1986 | Leiboff | |
| 4,675,948 A * | 6/1987 | Bengtsson | F16B 2/22 24/115 G |
| 4,712,549 A | 12/1987 | Peters et al. | |
| 4,741,336 A | 5/1988 | Failla et al. | |
| 4,778,468 A | 10/1988 | Hunt et al. | |
| 4,808,157 A | 2/1989 | Coombs | |
| 4,853,986 A | 8/1989 | Allen | |
| 4,878,269 A * | 11/1989 | Anscher | F16G 11/101 24/115 G |
| 5,108,420 A | 4/1992 | Marks | |
| 5,323,514 A * | 6/1994 | Masuda | F16G 11/101 24/115 G |
| 5,330,521 A | 7/1994 | Cohen | |
| 5,336,233 A | 8/1994 | Chen | |
| 5,350,399 A | 9/1994 | Erlebacher et al. | |
| 5,450,860 A | 9/1995 | O'Connor | |
| 5,473,812 A | 12/1995 | Morris et al. | |
| 5,643,289 A * | 7/1997 | Sauer | A61B 17/0469 29/282 |
| 5,776,178 A | 7/1998 | Pohndorf et al. | |
| 5,792,400 A | 8/1998 | Talja et al. | |
| 5,843,120 A | 12/1998 | Israel et al. | |
| 5,843,164 A | 12/1998 | Frantzen et al. | |
| 5,904,697 A | 5/1999 | Gifford, III et al. | |
| 5,948,000 A | 9/1999 | Larsen et al. | |
| 5,957,953 A | 9/1999 | DiPoto et al. | |
| 6,010,113 A | 1/2000 | Rotering | |
| 6,027,523 A | 2/2000 | Schmieding | |
| 6,045,497 A | 4/2000 | Schweich, Jr. et al. | |
| 6,193,734 B1 | 2/2001 | Bolduc et al. | |
| 6,206,913 B1 | 3/2001 | Yencho et al. | |
| 6,231,516 B1 | 5/2001 | Keilman et al. | |
| 6,298,272 B1 | 10/2001 | Peterfeso et al. | |
| 6,299,635 B1 | 10/2001 | Frantzen | |
| 6,332,893 B1 | 12/2001 | Mortier et al. | |
| 6,402,780 B2 | 6/2002 | Williamson, IV et al. | |
| 6,461,336 B1 | 10/2002 | Larre et al. | |
| 6,533,610 B1 | 3/2003 | Hankh et al. | |
| 6,575,976 B2 | 6/2003 | Grafton | |
| 6,602,288 B1 | 8/2003 | Cosgrove et al. | |
| 6,613,078 B1 | 9/2003 | Barone | |
| 6,613,079 B1 | 9/2003 | Wolinsky et al. | |
| 6,616,684 B1 | 9/2003 | Vidlund et al. | |
| 6,626,899 B2 | 9/2003 | Houser et al. | |
| 6,626,930 B1 | 9/2003 | Allen et al. | |
| 6,629,534 B1 | 10/2003 | St. Goar et al. | |
| 6,629,921 B1 | 10/2003 | Schweich, Jr. et al. | |
| 6,641,597 B2 | 11/2003 | Burkhart et al. | |
| 6,702,846 B2 | 3/2004 | Mikus et al. | |
| 6,723,038 B1 | 4/2004 | Schroeder et al. | |
| 6,730,118 B2 | 5/2004 | Spenser et al. | |
| 6,743,198 B1 | 6/2004 | Tihon | |
| 6,746,472 B2 | 6/2004 | Frazier et al. | |
| 6,776,754 B1 | 8/2004 | Wilk | |
| 6,797,001 B2 | 9/2004 | Mathis et al. | |
| 6,884,250 B2 | 4/2005 | Monassevitch et al. | |
| 6,908,478 B2 | 6/2005 | Alferness et al. | |
| 6,929,660 B1 | 8/2005 | Ainsworth et al. | |
| 7,018,406 B2 | 3/2006 | Seguin et al. | |
| 7,018,408 B2 | 3/2006 | Bailey et al. | |
| 7,037,290 B2 | 5/2006 | Gardeski et al. | |
| 7,041,097 B1 | 5/2006 | Webler | |
| 7,063,711 B1 | 6/2006 | Loshakove et al. | |
| 7,077,861 B2 | 7/2006 | Spence | |
| 7,101,395 B2 | 9/2006 | Tremulis et al. | |
| 7,101,396 B2 | 9/2006 | Artof et al. | |
| 7,125,421 B2 | 10/2006 | Tremulis et al. | |
| 7,144,363 B2 | 12/2006 | Pai et al. | |
| 7,159,593 B2 | 1/2007 | McCarthy et al. | |
| 7,166,127 B2 | 1/2007 | Spence et al. | |
| 7,169,187 B2 | 1/2007 | Datta et al. | |
| 7,175,625 B2 | 2/2007 | Culbert | |
| 7,179,282 B2 | 2/2007 | Alferness et al. | |
| 7,186,262 B2 | 3/2007 | Saadat | |
| 7,189,199 B2 | 3/2007 | McCarthy et al. | |
| 7,198,646 B2 | 4/2007 | Figulla et al. | |
| 7,201,772 B2 | 4/2007 | Schwammenthal et al. | |
| 7,211,107 B2 | 5/2007 | Bruckheimer et al. | |
| 7,258,697 B1 | 8/2007 | Cox et al. | |
| 7,311,697 B2 | 12/2007 | Osborne | |
| 7,311,728 B2 | 12/2007 | Solem et al. | |
| 7,316,706 B2 | 1/2008 | Bloom et al. | |
| 7,316,710 B1 | 1/2008 | Cheng et al. | |
| 7,329,279 B2 | 2/2008 | Haug et al. | |
| 7,335,213 B1 | 2/2008 | Hyde et al. | |
| 7,338,506 B2 | 3/2008 | Caro | |
| 7,351,256 B2 | 4/2008 | Hojeibane et al. | |
| 7,371,244 B2 | 5/2008 | Chatlynne et al. | |
| 7,374,573 B2 | 5/2008 | Gabbay | |
| 7,390,329 B2 | 6/2008 | Westra et al. | |
| 7,485,143 B2 | 2/2009 | Webler et al. | |
| 7,500,989 B2 | 3/2009 | Solem et al. | |
| 7,503,931 B2 | 3/2009 | Kowaisky et al. | |
| 7,510,575 B2 | 3/2009 | Spenser et al. | |
| 7,530,995 B2 | 5/2009 | Quijano et al. | |
| 7,547,321 B2 | 6/2009 | Silvestri et al. | |
| 7,549,983 B2 | 6/2009 | Roue et al. | |
| 7,597,703 B2 | 10/2009 | Sater | |
| 7,608,102 B2 | 10/2009 | Adams et al. | |
| 7,618,449 B2 | 11/2009 | Tremulis et al. | |
| 7,628,797 B2 | 12/2009 | Tieu et al. | |
| 7,632,303 B1 | 12/2009 | Stalker et al. | |
| 7,666,204 B2 | 2/2010 | Thornton et al. | |
| 7,758,632 B2 | 7/2010 | Hojeibane et al. | |
| 7,771,467 B2 | 8/2010 | Svensson | |
| 7,780,726 B2 | 8/2010 | Seguin | |
| 7,803,187 B2 | 9/2010 | Hauser | |
| 7,837,727 B2 | 11/2010 | Goetz et al. | |
| 7,857,846 B2 | 12/2010 | Alferness et al. | |
| 7,871,433 B2 | 1/2011 | Lattouf | |
| 7,942,927 B2 | 5/2011 | Kaye et al. | |
| 7,972,378 B2 | 7/2011 | Tabor et al. | |
| 7,991,484 B1 | 8/2011 | Sengupta et al. | |
| 7,992,567 B2 | 8/2011 | Hirotsuka et al. | |
| 7,993,368 B2 | 8/2011 | Gambale et al. | |
| 8,010,207 B2 | 8/2011 | Smits et al. | |

(56) References Cited

U.S. PATENT DOCUMENTS

| | | |
|---|---|---|
| 8,025,495 B2 | 9/2011 | Hardert et al. |
| 8,029,518 B2 | 10/2011 | Goldfarb et al. |
| 8,052,592 B2 | 11/2011 | Goldfarb et al. |
| 8,092,525 B2 | 1/2012 | Eliasen et al. |
| 8,108,054 B2 | 1/2012 | Helland |
| 8,109,996 B2 | 2/2012 | Stacchino et al. |
| 8,137,381 B2 | 3/2012 | Foerster et al. |
| 8,142,493 B2 | 3/2012 | Spence et al. |
| 8,142,495 B2 | 3/2012 | Hasenkam et al. |
| 8,147,542 B2 | 4/2012 | Maisano et al. |
| 8,157,810 B2 | 4/2012 | Case et al. |
| 8,172,898 B2 | 5/2012 | Alferness et al. |
| 8,197,441 B2 | 6/2012 | Webler et al. |
| 8,216,302 B2 | 7/2012 | Wilson et al. |
| 8,226,666 B2 * | 7/2012 | Zarbatany .......... A61B 17/0467 606/139 |
| 8,236,013 B2 | 8/2012 | Chu |
| 8,262,567 B2 | 9/2012 | Sharp et al. |
| 8,262,724 B2 | 9/2012 | Seguin et al. |
| 8,262,725 B2 | 9/2012 | Subramanian |
| 8,267,981 B2 | 9/2012 | Boock et al. |
| 8,323,335 B2 | 12/2012 | Rowe et al. |
| 8,332,051 B2 | 12/2012 | Sommer et al. |
| 8,398,672 B2 | 3/2013 | Kleshinski et al. |
| 8,449,606 B2 | 5/2013 | Ellasen et al. |
| 8,475,525 B2 | 7/2013 | Maisano et al. |
| 8,480,730 B2 | 7/2013 | Maurer et al. |
| 8,523,881 B2 | 9/2013 | Cabiri et al. |
| 8,545,553 B2 | 10/2013 | Zipory et al. |
| 8,628,569 B2 | 1/2014 | Benichou et al. |
| 8,628,571 B1 | 1/2014 | Hacohen et al. |
| 8,721,588 B2 | 5/2014 | Echarri et al. |
| 8,747,463 B2 | 6/2014 | Fogarty et al. |
| 8,784,481 B2 | 7/2014 | Alkhatib et al. |
| 8,790,394 B2 | 7/2014 | Miller et al. |
| 8,795,356 B2 | 8/2014 | Quadri et al. |
| 8,808,366 B2 | 8/2014 | Braido et al. |
| 8,852,272 B2 | 10/2014 | Gross et al. |
| 8,858,623 B2 | 10/2014 | Miller et al. |
| 8,870,949 B2 | 10/2014 | Rowe |
| 8,870,950 B2 | 10/2014 | Hacohen |
| 8,961,594 B2 | 2/2015 | Maisano et al. |
| 8,961,595 B2 | 2/2015 | Alkhatib |
| 8,961,596 B2 | 2/2015 | Maisano et al. |
| 8,979,922 B2 | 3/2015 | Jayasinghe et al. |
| 9,005,273 B2 | 4/2015 | Salahieh et al. |
| 9,017,296 B2 * | 4/2015 | Beck ..................... A61M 39/28 604/246 |
| 9,034,032 B2 | 5/2015 | McLean et al. |
| 9,034,033 B2 | 5/2015 | McLean et al. |
| 9,241,702 B2 | 1/2016 | Maisano et al. |
| 9,326,870 B2 | 5/2016 | Berglund et al. |
| 2002/0013571 A1 | 1/2002 | Goldfarb et al. |
| 2002/0032481 A1 | 3/2002 | Gabbay |
| 2002/0082625 A1 | 6/2002 | Huxel et al. |
| 2002/0107564 A1 | 8/2002 | Cox et al. |
| 2002/0151961 A1 | 10/2002 | Lashinski et al. |
| 2002/0156517 A1 | 10/2002 | Perouse |
| 2002/0177904 A1 | 11/2002 | Huxel et al. |
| 2003/0033003 A1 | 2/2003 | Harrison et al. |
| 2003/0057156 A1 | 3/2003 | Peterson et al. |
| 2003/0083742 A1 | 5/2003 | Spence et al. |
| 2003/0093096 A1 | 5/2003 | McGuckin, Jr. et al. |
| 2003/0167071 A1 | 9/2003 | Martin et al. |
| 2003/0229350 A1 | 12/2003 | Kay |
| 2003/0229361 A1 * | 12/2003 | Jackson ............. A61B 17/0487 606/144 |
| 2003/0236568 A1 | 12/2003 | Hojelbane et al. |
| 2004/0117009 A1 | 6/2004 | Cali et al. |
| 2004/0133274 A1 | 7/2004 | Webler et al. |
| 2004/0181287 A1 | 9/2004 | Gellman |
| 2004/0186566 A1 | 9/2004 | Hindrichs et al. |
| 2004/0193092 A1 | 9/2004 | Deal |
| 2004/0236419 A1 | 11/2004 | Milo |
| 2004/0260389 A1 | 12/2004 | Case et al. |
| 2005/0004668 A1 | 1/2005 | Aklog et al. |
| 2005/0016560 A1 | 1/2005 | Voughlohn |
| 2005/0021085 A1 | 1/2005 | Abrams et al. |
| 2005/0055089 A1 | 3/2005 | Macoviak et al. |
| 2005/0059997 A1 | 3/2005 | Bauman et al. |
| 2005/0075723 A1 | 4/2005 | Schroeder et al. |
| 2005/0080483 A1 | 4/2005 | Solem et al. |
| 2005/0090827 A1 | 4/2005 | Gedebou |
| 2005/0096666 A1 | 5/2005 | Gordon et al. |
| 2005/0107812 A1 | 5/2005 | Starksen et al. |
| 2005/0107871 A1 | 5/2005 | Realyvasquez et al. |
| 2005/0113900 A1 | 5/2005 | Shiroff et al. |
| 2005/0125077 A1 | 6/2005 | Harmon et al. |
| 2005/0137688 A1 | 6/2005 | Salahieh et al. |
| 2005/0137695 A1 | 6/2005 | Salahieh et al. |
| 2005/0154448 A1 | 7/2005 | Cully et al. |
| 2005/0177180 A1 | 8/2005 | Kaganov et al. |
| 2005/0177228 A1 | 8/2005 | Solem et al. |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222666 A1 | 10/2005 | Aranyi |
| 2005/0251208 A1 | 11/2005 | Elmer et al. |
| 2005/0256532 A1 | 11/2005 | Nayak et al. |
| 2005/0273138 A1 | 12/2005 | To et al. |
| 2005/0283246 A1 | 12/2005 | Cauthen, III et al. |
| 2006/0004442 A1 | 1/2006 | Spenser et al. |
| 2006/0020326 A9 | 1/2006 | Bolduc et al. |
| 2006/0020327 A1 | 1/2006 | Lashinski et al. |
| 2006/0052821 A1 | 3/2006 | Abbott et al. |
| 2006/0106420 A1 | 5/2006 | Dolan et al. |
| 2006/0106423 A1 | 5/2006 | Weisel et al. |
| 2006/0129166 A1 | 6/2006 | Lavelle |
| 2006/0161265 A1 | 7/2006 | Levine et al. |
| 2006/0173524 A1 | 8/2006 | Salahieh et al. |
| 2006/0178700 A1 | 8/2006 | Quinn |
| 2006/0200199 A1 | 9/2006 | Bonutti et al. |
| 2006/0206201 A1 | 9/2006 | Garcia et al. |
| 2006/0229708 A1 | 10/2006 | Powell et al. |
| 2006/0241745 A1 | 10/2006 | Solem |
| 2006/0241748 A1 | 10/2006 | Lee et al. |
| 2006/0259044 A1 * | 11/2006 | Onuki ................. A61B 17/0401 606/139 |
| 2006/0259135 A1 | 11/2006 | Navia et al. |
| 2006/0259137 A1 | 11/2006 | Artof et al. |
| 2006/0276871 A1 | 12/2006 | Lamson et al. |
| 2006/0282161 A1 | 12/2006 | Huynh et al. |
| 2007/0005081 A1 * | 1/2007 | Findlay, III ........ A61B 17/0467 606/148 |
| 2007/0010829 A1 * | 1/2007 | Nobles ............... A61B 17/0485 606/148 |
| 2007/0016237 A1 | 1/2007 | Cartledge et al. |
| 2007/0016268 A1 | 1/2007 | Gurskis et al. |
| 2007/0021781 A1 * | 1/2007 | Jervis ................. A61B 17/0487 606/232 |
| 2007/0032787 A1 | 2/2007 | Hassett et al. |
| 2007/0038221 A1 | 2/2007 | Fine et al. |
| 2007/0038296 A1 | 2/2007 | Navia et al. |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055340 A1 | 3/2007 | Pryor |
| 2007/0060895 A1 | 3/2007 | Sibbitt, Jr. et al. |
| 2007/0060989 A1 | 3/2007 | Deem et al. |
| 2007/0061010 A1 | 3/2007 | Hauser et al. |
| 2007/0066863 A1 | 3/2007 | Rafiee et al. |
| 2007/0083168 A1 | 4/2007 | Whiting et al. |
| 2007/0093869 A1 | 4/2007 | Bloom et al. |
| 2007/0100427 A1 | 5/2007 | Perouse |
| 2007/0112425 A1 | 5/2007 | Schaller et al. |
| 2007/0118151 A1 | 5/2007 | Davidson |
| 2007/0123936 A1 | 5/2007 | Goldin et al. |
| 2007/0162107 A1 | 7/2007 | Haug et al. |
| 2007/0168013 A1 | 7/2007 | Douglas |
| 2007/0179530 A1 * | 8/2007 | Tieu .................... A61B 17/0487 606/232 |
| 2007/0185532 A1 | 8/2007 | Stone et al. |
| 2007/0198082 A1 | 8/2007 | Kapadia et al. |
| 2007/0203391 A1 | 8/2007 | Bloom et al. |

(56) References Cited

U.S. PATENT DOCUMENTS

| | | |
|---|---|---|
| 2007/0208389 A1 | 9/2007 | Amundson et al. |
| 2007/0219558 A1 | 9/2007 | Deutsch et al. |
| 2007/0250160 A1 | 10/2007 | Rafiee |
| 2007/0265700 A1 | 11/2007 | Eliasen et al. |
| 2007/0270943 A1 | 11/2007 | Solem et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0288089 A1 | 12/2007 | Gurskis et al. |
| 2008/0003539 A1 | 1/2008 | Lundgren |
| 2008/0015617 A1 | 1/2008 | Harari et al. |
| 2008/0027268 A1 | 1/2008 | Buckner et al. |
| 2008/0027446 A1 | 1/2008 | Stone et al. |
| 2008/0027483 A1 | 1/2008 | Cartledge et al. |
| 2008/0035160 A1 | 2/2008 | Woodson et al. |
| 2008/0058866 A1 | 3/2008 | Young et al. |
| 2008/0077231 A1 | 3/2008 | Heringes et al. |
| 2008/0097595 A1 | 4/2008 | Gabbay |
| 2008/0125861 A1 | 5/2008 | Webler et al. |
| 2008/0140116 A1 | 6/2008 | Bonutti |
| 2008/0167714 A1 | 7/2008 | St. Goar et al. |
| 2008/0190989 A1 | 8/2008 | Crews et al. |
| 2008/0234729 A1* | 9/2008 | Page ............... A61B 17/0485 606/232 |
| 2008/0262598 A1 | 10/2008 | Elmaleh |
| 2008/0262609 A1 | 10/2008 | Gross et al. |
| 2008/0275469 A1 | 11/2008 | Fanton et al. |
| 2008/0281411 A1 | 11/2008 | Berreklouw |
| 2008/0288044 A1 | 11/2008 | Osborne |
| 2008/0288062 A1 | 11/2008 | Andrieu et al. |
| 2008/0300629 A1 | 12/2008 | Surti |
| 2009/0005792 A1* | 1/2009 | Miyamoto ......... A61B 17/0487 606/139 |
| 2009/0005863 A1 | 1/2009 | Goetz et al. |
| 2009/0043382 A1 | 2/2009 | Maurer et al. |
| 2009/0048668 A1 | 2/2009 | Wilson et al. |
| 2009/0082828 A1 | 3/2009 | Ostroff |
| 2009/0082847 A1 | 3/2009 | Zacharias et al. |
| 2009/0084386 A1 | 4/2009 | McClellan et al. |
| 2009/0094798 A1* | 4/2009 | Yao .................... A43C 1/00 24/115 G |
| 2009/0099647 A1 | 4/2009 | Glimsdale et al. |
| 2009/0099649 A1 | 4/2009 | Chobotov et al. |
| 2009/0112052 A1 | 4/2009 | Lund et al. |
| 2009/0118776 A1 | 5/2009 | Kelsch et al. |
| 2009/0131849 A1 | 5/2009 | Maurer et al. |
| 2009/0132033 A1 | 5/2009 | Maurer et al. |
| 2009/0143808 A1 | 6/2009 | Houser |
| 2009/0149872 A1 | 6/2009 | Gross et al. |
| 2009/0171439 A1 | 7/2009 | Nissl |
| 2009/0216265 A1 | 8/2009 | DeVries et al. |
| 2009/0240326 A1 | 9/2009 | Wilson et al. |
| 2009/0254103 A1 | 10/2009 | Deutsch |
| 2009/0259307 A1 | 10/2009 | Gross et al. |
| 2009/0264991 A1 | 10/2009 | Paul, Jr. et al. |
| 2009/0264995 A1 | 10/2009 | Subramanian |
| 2009/0276040 A1 | 11/2009 | Rowe et al. |
| 2009/0287304 A1 | 11/2009 | Dahlgren et al. |
| 2009/0326648 A1 | 12/2009 | Machold et al. |
| 2010/0022948 A1 | 1/2010 | Wilson et al. |
| 2010/0023117 A1 | 1/2010 | Yoganathan et al. |
| 2010/0023118 A1 | 1/2010 | Medlock et al. |
| 2010/0029071 A1 | 2/2010 | Russell et al. |
| 2010/0030329 A1 | 2/2010 | Frater |
| 2010/0049293 A1 | 2/2010 | Zukowski et al. |
| 2010/0063520 A1 | 3/2010 | Bilotti |
| 2010/0063542 A1 | 3/2010 | van der Burg et al. |
| 2010/0063586 A1 | 3/2010 | Hasenkam et al. |
| 2010/0121349 A1 | 5/2010 | Meier et al. |
| 2010/0121434 A1 | 5/2010 | Paul et al. |
| 2010/0121435 A1 | 5/2010 | Subramanian et al. |
| 2010/0130992 A1 | 5/2010 | Machold et al. |
| 2010/0161041 A1 | 6/2010 | Maisano et al. |
| 2010/0161042 A1 | 6/2010 | Maisano et al. |
| 2010/0161043 A1 | 6/2010 | Maisano et al. |
| 2010/0161047 A1 | 6/2010 | Cabiri |
| 2010/0168791 A1 | 7/2010 | Kassab et al. |
| 2010/0174358 A1 | 7/2010 | Rabkin et al. |
| 2010/0185278 A1 | 7/2010 | Schankereli |
| 2010/0204662 A1 | 8/2010 | Orlov et al. |
| 2010/0211166 A1 | 8/2010 | Miller et al. |
| 2010/0217382 A1 | 8/2010 | Chau et al. |
| 2010/0228269 A1 | 9/2010 | Garrison et al. |
| 2010/0234935 A1 | 9/2010 | Bashiri et al. |
| 2010/0249908 A1 | 9/2010 | Chau et al. |
| 2010/0264192 A1 | 10/2010 | Marczyk |
| 2010/0268204 A1 | 10/2010 | Tieu et al. |
| 2010/0280603 A1 | 11/2010 | Maisano et al. |
| 2010/0280604 A1 | 11/2010 | Zipory et al. |
| 2010/0280605 A1 | 11/2010 | Hammer et al. |
| 2010/0286628 A1 | 11/2010 | Gross |
| 2010/0286767 A1 | 11/2010 | Zipory et al. |
| 2010/0298930 A1 | 11/2010 | Orlov |
| 2010/0324598 A1 | 12/2010 | Anderson |
| 2010/0324668 A1 | 12/2010 | Maurer et al. |
| 2011/0004296 A1 | 1/2011 | Lutter et al. |
| 2011/0009818 A1 | 1/2011 | Goff |
| 2011/0011917 A1 | 1/2011 | Loulmet |
| 2011/0022164 A1 | 1/2011 | Quinn et al. |
| 2011/0029066 A1 | 2/2011 | Gilad et al. |
| 2011/0029071 A1 | 2/2011 | Ziotnick et al. |
| 2011/0035000 A1 | 2/2011 | Nieminen et al. |
| 2011/0040366 A1 | 2/2011 | Goetz et al. |
| 2011/0071626 A1 | 3/2011 | Wright et al. |
| 2011/0077733 A1 | 3/2011 | Solem |
| 2011/0082538 A1 | 4/2011 | Dahlgren et al. |
| 2011/0087146 A1 | 4/2011 | Ryan et al. |
| 2011/0092993 A1 | 4/2011 | Jacobs |
| 2011/0093002 A1 | 4/2011 | Rucker et al. |
| 2011/0098732 A1 | 4/2011 | Jacobs |
| 2011/0106245 A1 | 5/2011 | Miller et al. |
| 2011/0106247 A1 | 5/2011 | Miller et al. |
| 2011/0112619 A1 | 5/2011 | Foster et al. |
| 2011/0112632 A1 | 5/2011 | Chau et al. |
| 2011/0137397 A1 | 6/2011 | Chau et al. |
| 2011/0152889 A1* | 6/2011 | Ashland ............ A61B 17/0487 606/144 |
| 2011/0152998 A1 | 6/2011 | Berez et al. |
| 2011/0166636 A1 | 7/2011 | Rowe |
| 2011/0184510 A1 | 7/2011 | Maisano et al. |
| 2011/0190879 A1 | 8/2011 | Bobo et al. |
| 2011/0208283 A1 | 8/2011 | Rust |
| 2011/0224785 A1 | 9/2011 | Hacohen |
| 2011/0238088 A1 | 9/2011 | Bolduc et al. |
| 2011/0238112 A1 | 9/2011 | Kim et al. |
| 2011/0251641 A1* | 10/2011 | Sauer ................ A61B 17/0487 606/230 |
| 2011/0251678 A1 | 10/2011 | Eidenschink et al. |
| 2011/0264208 A1 | 10/2011 | Duffy et al. |
| 2011/0301698 A1 | 12/2011 | Miller et al. |
| 2012/0016343 A1 | 1/2012 | Gill |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0035712 A1 | 2/2012 | Maisano et al. |
| 2012/0059414 A1* | 3/2012 | Roorda ............. A61B 17/0057 606/232 |
| 2012/0083806 A1 | 4/2012 | Goertzen |
| 2012/0123531 A1 | 5/2012 | Tsukashima et al. |
| 2012/0130374 A1 | 5/2012 | Bouduban et al. |
| 2012/0130421 A1 | 5/2012 | Hafez et al. |
| 2012/0143320 A1 | 6/2012 | Eliasen et al. |
| 2012/0158053 A1 | 6/2012 | Paulos |
| 2012/0179244 A1 | 7/2012 | Schankereli et al. |
| 2012/0215236 A1 | 8/2012 | Matsunaga et al. |
| 2012/0222969 A1 | 9/2012 | Osborne et al. |
| 2012/0226349 A1 | 9/2012 | Tuval et al. |
| 2012/0232373 A1 | 9/2012 | Hallander et al. |
| 2012/0245604 A1 | 9/2012 | Tegzes |
| 2012/0283757 A1 | 11/2012 | Miller et al. |
| 2012/0296349 A1 | 11/2012 | Smith et al. |
| 2012/0310328 A1 | 12/2012 | Olson et al. |
| 2013/0030522 A1 | 1/2013 | Rowe et al. |
| 2013/0041459 A1 | 2/2013 | Wilson et al. |

(56) References Cited

U.S. PATENT DOCUMENTS

| | | |
|---|---|---|
| 2013/0053951 A1 | 2/2013 | Ruyra Baliarda |
| 2013/0085529 A1 | 4/2013 | Housman |
| 2013/0096664 A1 | 4/2013 | Goetz et al. |
| 2013/0096672 A1 | 4/2013 | Reich et al. |
| 2013/0166017 A1 | 6/2013 | Cartledge et al. |
| 2013/0166022 A1 | 6/2013 | Conklin |
| 2013/0172978 A1 | 7/2013 | Vidlund et al. |
| 2013/0231701 A1* | 9/2013 | Voss ............... A61B 17/0057 606/232 |
| 2013/0281760 A1 | 10/2013 | Farnan et al. |
| 2013/0296925 A1 | 11/2013 | Chanduszko et al. |
| 2013/0331930 A1 | 12/2013 | Rowe et al. |
| 2014/0005778 A1 | 1/2014 | Buchbinder et al. |
| 2014/0018911 A1 | 1/2014 | Zhou et al. |
| 2014/0031928 A1 | 1/2014 | Murphy et al. |
| 2014/0058405 A1 | 2/2014 | Foster |
| 2014/0114390 A1 | 4/2014 | Tobis et al. |
| 2014/0121763 A1 | 5/2014 | Duffy et al. |
| 2014/0142689 A1 | 5/2014 | De Canniere et al. |
| 2014/0163690 A1 | 6/2014 | White |
| 2014/0200657 A1 | 7/2014 | Maurer et al. |
| 2014/0207231 A1 | 7/2014 | Hacohen et al. |
| 2014/0214159 A1 | 7/2014 | Vidlund et al. |
| 2014/0243894 A1 | 8/2014 | Groothuis et al. |
| 2014/0257475 A1 | 9/2014 | Gross et al. |
| 2014/0288639 A1 | 9/2014 | Gainor |
| 2014/0296962 A1 | 10/2014 | Cartledge et al. |
| 2014/0309730 A1 | 10/2014 | Alon et al. |
| 2014/0324164 A1 | 10/2014 | Gross et al. |
| 2014/0358224 A1 | 12/2014 | Tegels et al. |
| 2014/0379006 A1 | 12/2014 | Sutherland et al. |
| 2014/0379074 A1 | 12/2014 | Spence et al. |
| 2014/0379076 A1 | 12/2014 | Vidlund et al. |
| 2015/0018940 A1 | 1/2015 | Quill et al. |
| 2015/0045879 A1 | 2/2015 | Longoria et al. |
| 2015/0051698 A1 | 2/2015 | Ruyra Baliarda et al. |
| 2015/0073545 A1 | 3/2015 | Braido |
| 2015/0094800 A1 | 4/2015 | Chawla |
| 2015/0094802 A1 | 4/2015 | Buchbinder et al. |
| 2015/0100116 A1 | 4/2015 | Mohl et al. |
| 2015/0119936 A1 | 4/2015 | Gilmore et al. |
| 2015/0127097 A1 | 5/2015 | Neumann et al. |
| 2015/0142103 A1 | 5/2015 | Vidlund |
| 2015/0182336 A1 | 7/2015 | Zipory et al. |
| 2015/0223934 A1 | 8/2015 | Vidlund et al. |
| 2015/0250590 A1 | 9/2015 | Gries et al. |
| 2015/0272730 A1 | 10/2015 | Melnick et al. |
| 2016/0242762 A1 | 8/2016 | Gilmore et al. |
| 2016/0262741 A1 | 9/2016 | Gilmore et al. |

FOREIGN PATENT DOCUMENTS

| | | |
|---|---|---|
| EP | 1759663 A2 | 3/2007 |
| EP | 1836971 A2 | 9/2007 |
| EP | 1968491 B1 | 9/2008 |
| WO | 92/05093 A1 | 4/1992 |
| WO | 97/41778 A1 | 11/1997 |
| WO | 00/28923 A1 | 5/2000 |
| WO | 01/10306 A1 | 2/2001 |
| WO | 2004/069055 A2 | 8/2004 |
| WO | 2004/082538 A2 | 9/2004 |
| WO | 2005/012063 A2 | 3/2005 |
| WO | 2005/102194 A2 | 11/2005 |
| WO | 2006/097931 A2 | 9/2006 |
| WO | 2007/080595 A2 | 7/2007 |
| WO | 2009/039400 A1 | 3/2009 |
| WO | 2009/101617 A2 | 8/2009 |
| WO | 2010/004546 A1 | 1/2010 |
| WO | 2010/008549 A1 | 1/2010 |
| WO | 2010/071494 A1 | 6/2010 |
| WO | 2010/073246 A2 | 7/2010 |
| WO | 2010/128502 A1 | 11/2010 |
| WO | 2010/128503 A2 | 11/2010 |
| WO | 2011/051942 A1 | 5/2011 |
| WO | 2011/089601 A1 | 7/2011 |
| WO | 2011/143263 A2 | 11/2011 |
| WO | 2012/127309 A4 | 9/2012 |
| WO | 2013/003228 A1 | 1/2013 |
| WO | 2013/011502 A2 | 1/2013 |
| WO | 2013/028145 A1 | 2/2013 |
| WO | 2013/078497 A1 | 6/2013 |
| WO | 2014/064694 A2 | 5/2014 |
| WO | 2014/087402 A1 | 6/2014 |
| WO | 2014/108903 A1 | 7/2014 |
| WO | 2014/141239 A1 | 9/2014 |
| WO | 2015/015497 A1 | 2/2015 |
| WO | 2015/063580 A2 | 5/2015 |
| WO | 2015/193728 A2 | 12/2015 |
| WO | 2016/087934 A1 | 6/2016 |

OTHER PUBLICATIONS

Ottavio Alfieri, et al; "An Effective Technique to Correct Anterior Mitral Leaflet Prolapse", Journal of Cardiac Surgery, vol. 14, Pt. 6, pp. 468-470; Nov.-Dec. 1999.

Ottavio Alfieri, et al, "The double-orifice technique in mitral valve repair: A simple solution for complex problems", The Journal of Thoracic and Cardiovascular Surgery, vol. 122, pp. 674-681; Oct. 2001.

Ottavio Alfieri, et al; "Novel Suture Device for Beating-Heart Mitral Leaflet Approximation", Ann. Thorac Surg; vol. 74; pp. 1488-1493; Nov. 2002.

Amplatzer; Cardiac Plug Brochure (English Pages), AGA Medical Corporation, Plymouth, MN Copyright 2008-2011, downloaded Jan. 11, 2011.

Brian S. Beale; "Surgical Repair of Collateral Ligament Injuries", presented at the 63rd CVMA Convention, Halifax, Nova Scotia, Canada, Jul. 6-9, 2011, 4 pages.

"Spinal & Epidural Needles", downloaded on Feb. 18, 2016 from http://www.cothon.net/Anestesi_Obstetrica/Neuroaxial_needles.html.

Dentistry Today; "Implant Direct" product information page, Jun. 1, 2011, downloaded Dec. 10, 2012 from http://dentistrytoday.com/top25implant-i/5558-implant-direct.

Francesco Maisano, et al; "The double-orifice technique as a standardized approach to treat mitral regurgitation due to severy myxomatous disease: surgical technique", European Journal of Cardio Thoracic Surgery 17. pp. 201-205, Mar. 2000.

Smith & Nephew Minitac™T12.0 Suture Anchor Product Description, downloaded on Dec. 9, 2012 from http://global.smith-nephew.com/us/MINITAC_TI_2_SUTURE_ANCHR_3127.htm.

Extended European Search Report dated Apr. 10, 2015; Appln. No. 11734451.5-1662 / 2525741 PCT/IL2011000064.

Extended European Search Report dated May 15, 2015; Appln. No. 12814417.7-1506/ 2734157 PCT/IL2012000282.

Invitation to Pay Additional Fees; PCT/IB2014/002351 dated Apr. 20, 2015.

Invitation to Pay Additional Fees: PCT/IL2014/050027 dated Apr. 4, 2014.

Invitation to Pay Additional Fees: PCT/IB15/01196 dated Oct. 26, 2015.

Invitation to Pay Additional Fees: PCT/IB2016/000840 dated Oct. 13, 2016.

International Search Report and Written Opinon dated May 19, 2011; PCT/IL11/00064.

International Search Report and Written Opinion dated Jan. 22, 2013; PCT/IL2012000282.

International Search Report and Written Opinion dated Dec. 6, 2013; PCT/IL2013/050470.

International Search Report and Written Opinion dated Mar. 17, 2014; PCT/IL1350937.

International Search Report and Written Opinion dated Jun. 30, 2014; PCT/IL2014/050233.

International Search Report and Written Opinion dated Jun. 10, 2015; PCT/IB2014/002351.

International Search Report and Written Opinion dated May 28, 2014; PCT/IL2014/050027.

(56) References Cited

OTHER PUBLICATIONS

International Search Report and Written Opinion dated Jan. 8, 2016; PCT/IB15/01106.
International Search Report and Written Opinion dated Apr. 15, 2016; PCT/IB2015/002354.
First Chinese Office Action dated Jun. 23, 2016; Appln. No. 201480028044.3.
Chinese Patent Office Notice of Allowance dated Sep. 5, 2016; Appln. No. 201480028044.3.
First Chinese Office Action dated Jun. 30, 2014; Appln. No. 201180015301.6.
Second Chinese Office Action dated Feb. 10, 2015; Appln. No. 201180015301.6.
Third Chinese Office Action dated Jun. 30, 2015; Appln. No. 201180015301.6.
Japanese Office Action dated Oct. 28, 2014; Appln. No. 2012-549463.
Japanese Office Action dated Jul. 7, 2015; Appln. No. 2012-549463.
USPTO NFOA dated Jul. 6, 2012 in connection with U.S. Appl. No. 12/692,061.
USPTO Interview Summary dated Nov. 5, 2012 in connection with U.S. Appl. No. 12/692,061.
USPTO NOA dated Mar. 6, 2013 in connection with U.S. Appl. No. 12/692,061.
USPTO NOA dated May 10, 2013 in connection with U.S. Appl. No. 12/692,061.
USPTO NOA dated Dec. 4, 2014 in connection with U.S. Appl. No. 13/188,175.
USPTO NFOA dated Dec. 5, 2013 in connection with U.S. Appl. No. 13/485,145.
USPTO FOA dated Jul. 7, 2014 in connection with U.S. Appl. No. 13/485,145.
USPTO FOA dated Sep. 25, 2014 in connection with U.S. Appl. No. 13/485,145.
USPTO NOA dated Dec. 9, 2014 in connection with U.S. Appl. No. 13/485,145.
USPTO NFOA dated Nov. 25, 2014 in connection with U.S. Appl. No. 13/553,081.
USPTO NOA dated Sep. 14, 2015 in connection with U.S. Appl. No. 13/553,081.
USPTO RR dated Feb. 25, 2015 in connection with U.S. Appl. No. 13/574,088.
USPTO NFOA dated Oct. 7, 2015 in connection with U.S. Appl. No. 13/574,088.
USPTO FOA dated May 11, 2016 in connection with U.S. Appl. No. 13/574,088.
USPTO NFOA dated Sep. 14, 2016 in connection with U.S. Appl. No. 13/574,088.
USPTO RR dated Feb. 2, 2015 in connection with U.S. Appl. No. 14/143,355.
USPTO NOA dated Sep. 24, 2015 in connection with U.S. Appl. No. 14/143,355.
USPTO NOA dated Dec. 4, 2015 in connection with U.S. Appl. No. 14/143,355.
USPTO NFOA dated Apr. 18, 2016 in connection with U.S. Appl. No. 14/584,286.
U.S. Appl. No. 60/902,146, filed Feb. 16, 2007.
U.S. Appl. No. 62/014,397, filed Jun. 19, 2014.
U.S. Appl. No. 62/086,269, filed Dec. 2, 2014.
U.S. Appl. No. 62/167,660, filed May 28, 2015.
U.S. Appl. No. 62/131,636, filed Mar. 11, 2016.

* cited by examiner

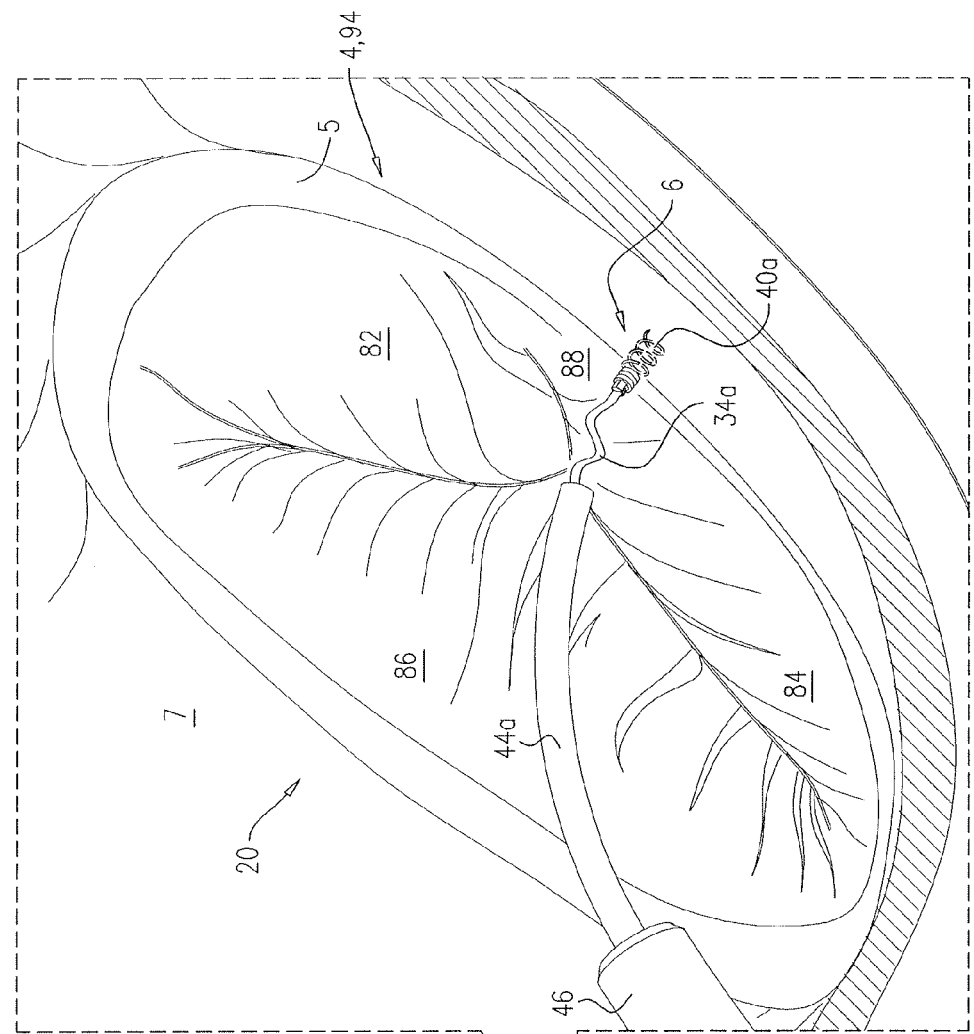
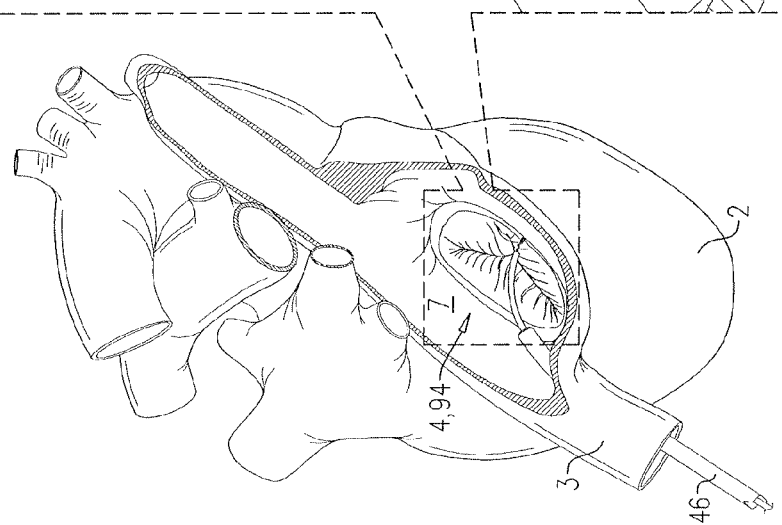
FIG. 3

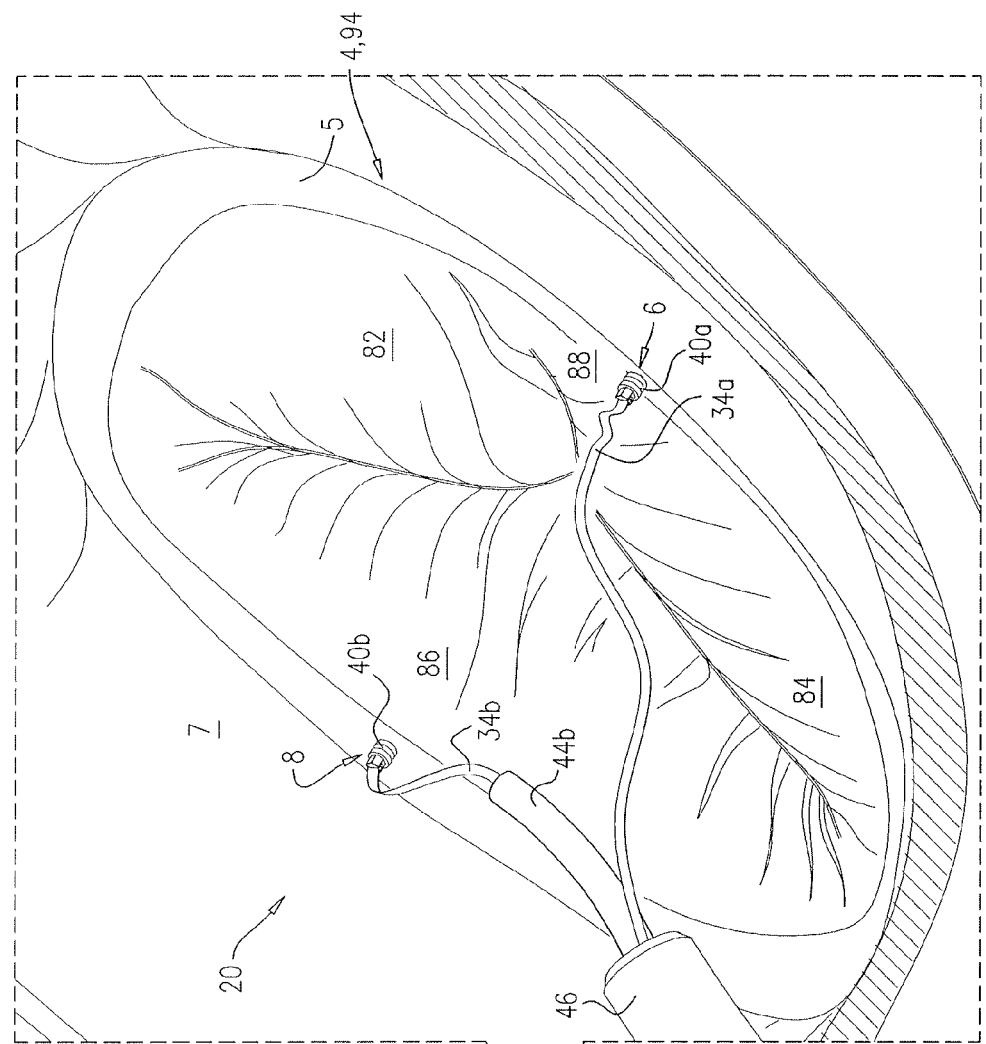
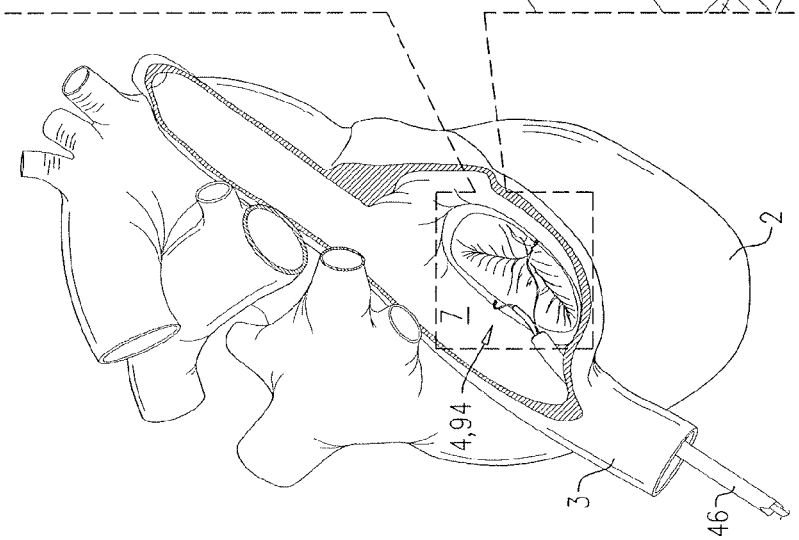
FIG. 4

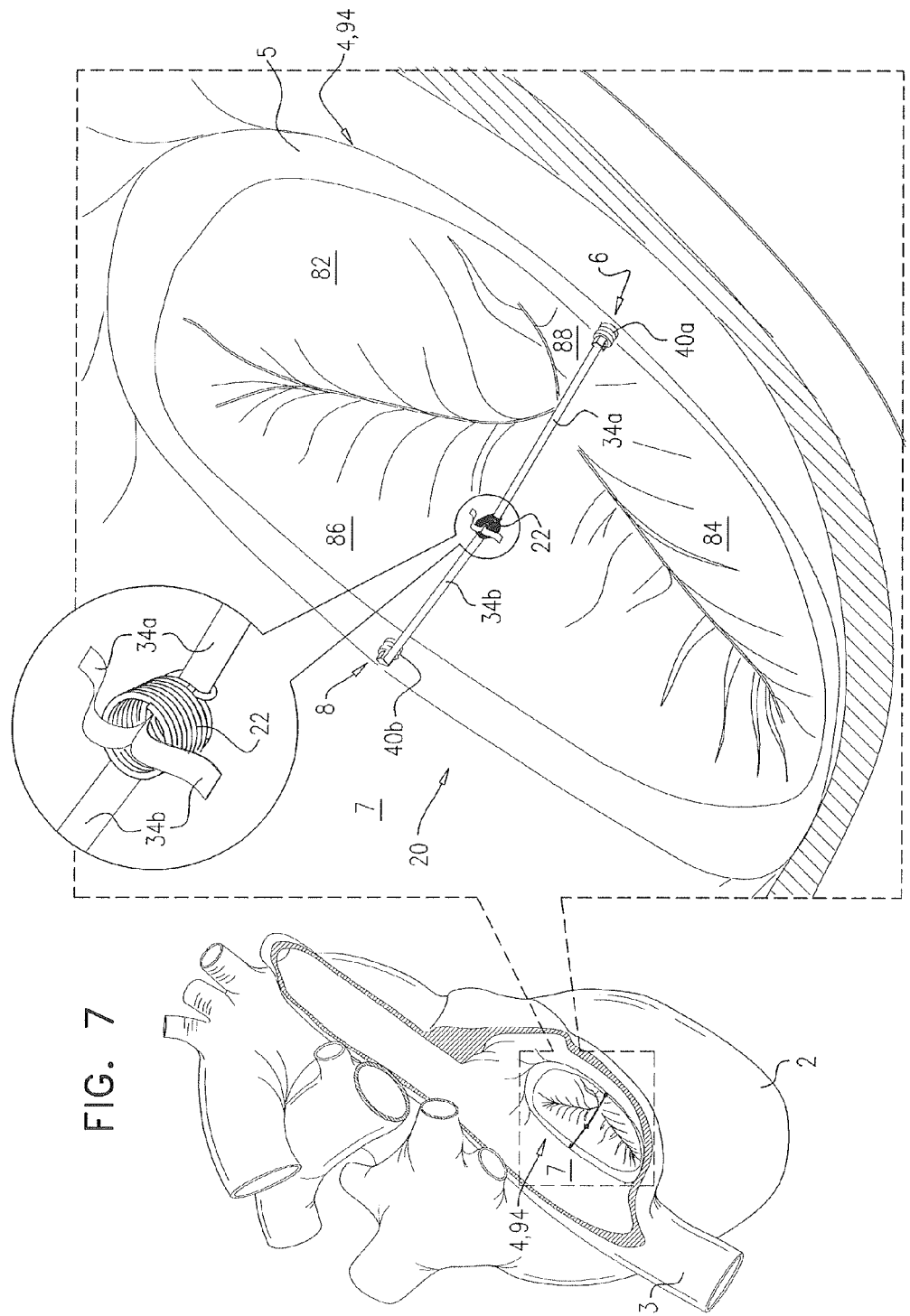

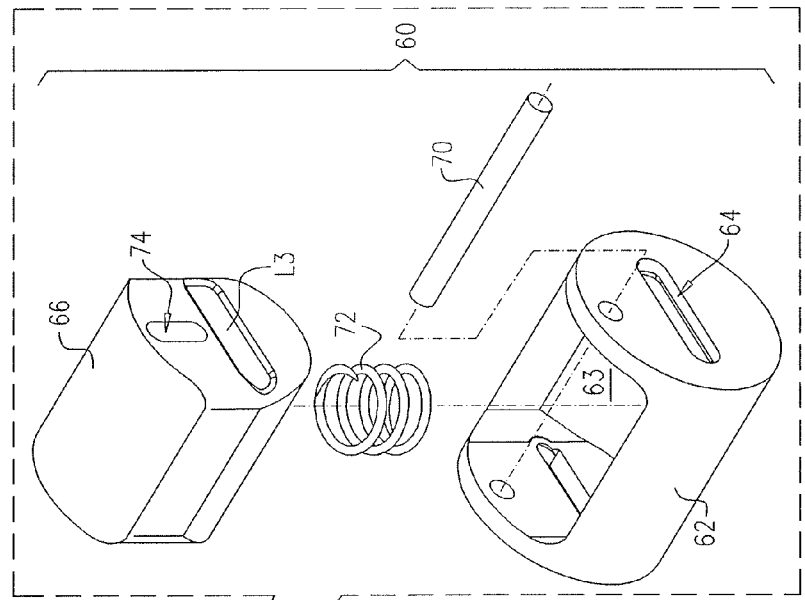
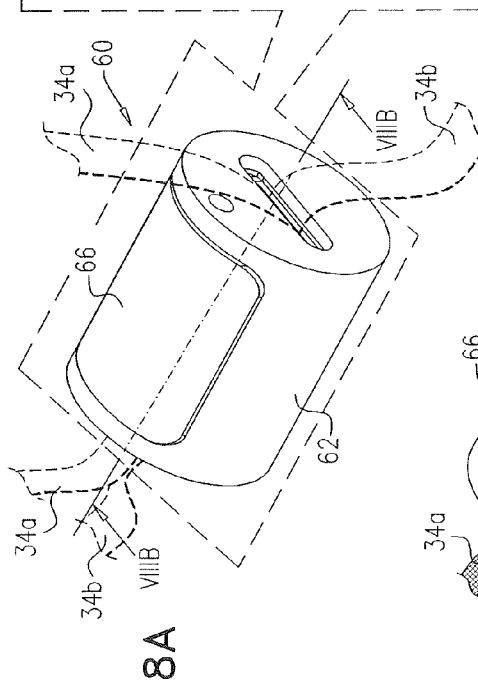
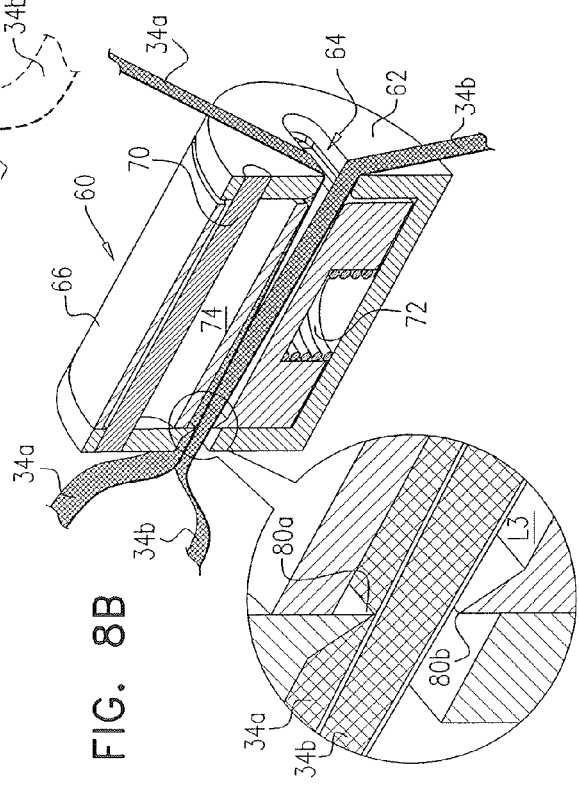
FIG. 8A
FIG. 8B

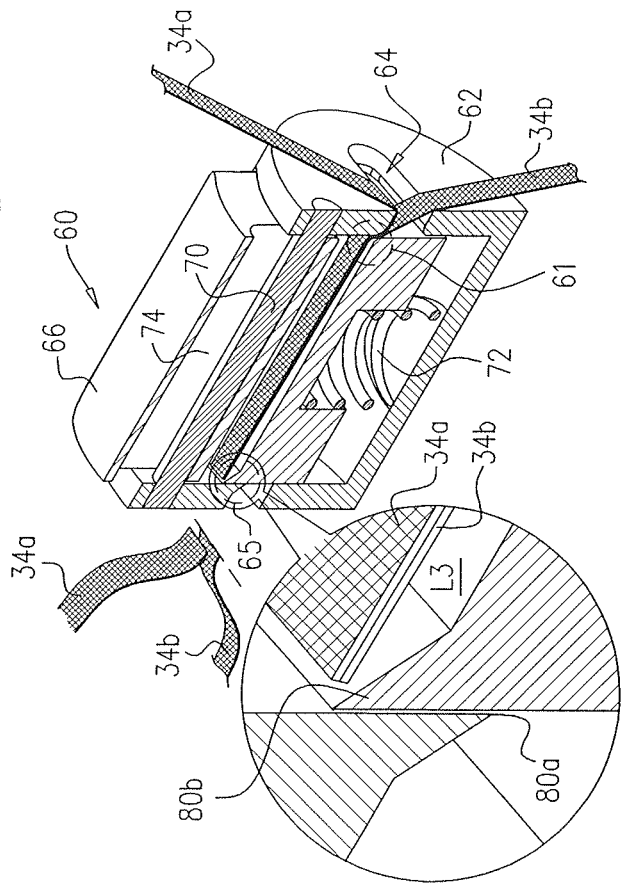
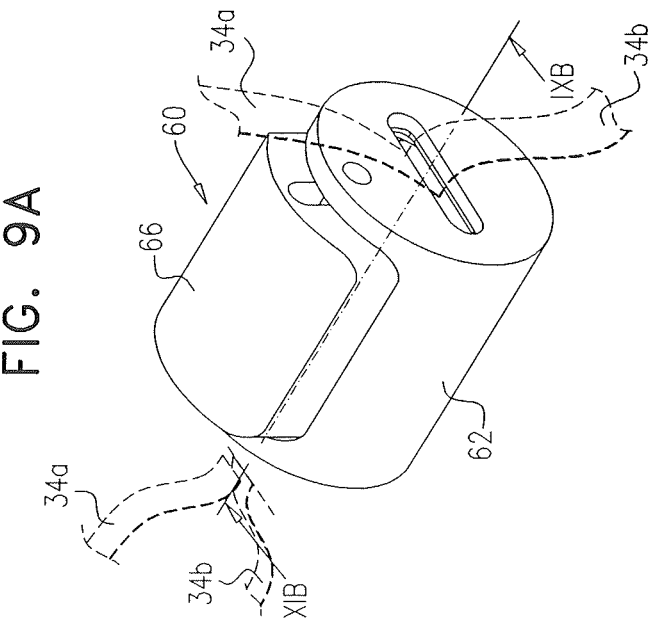
FIG. 9B
FIG. 9A

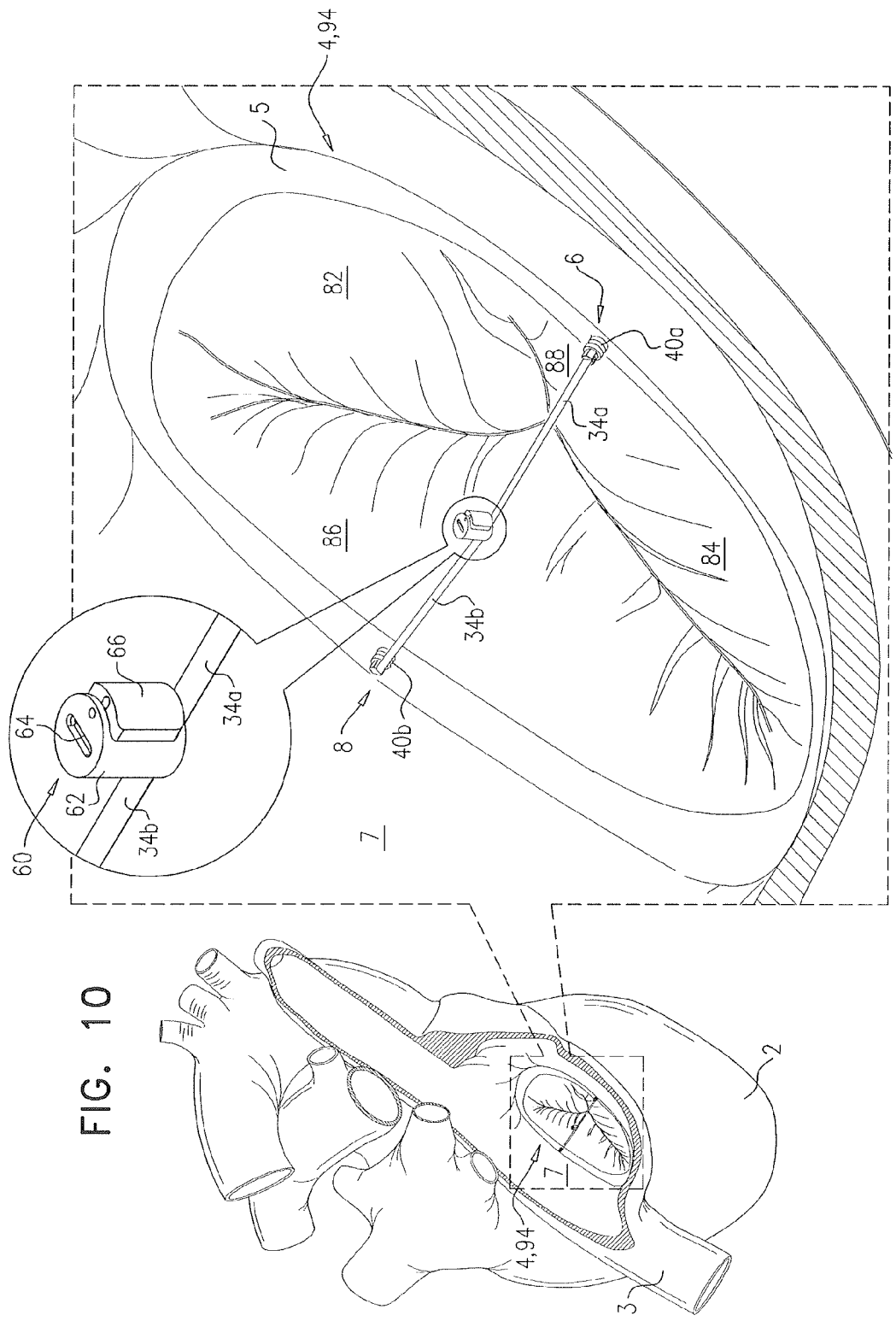

FIG. 11A
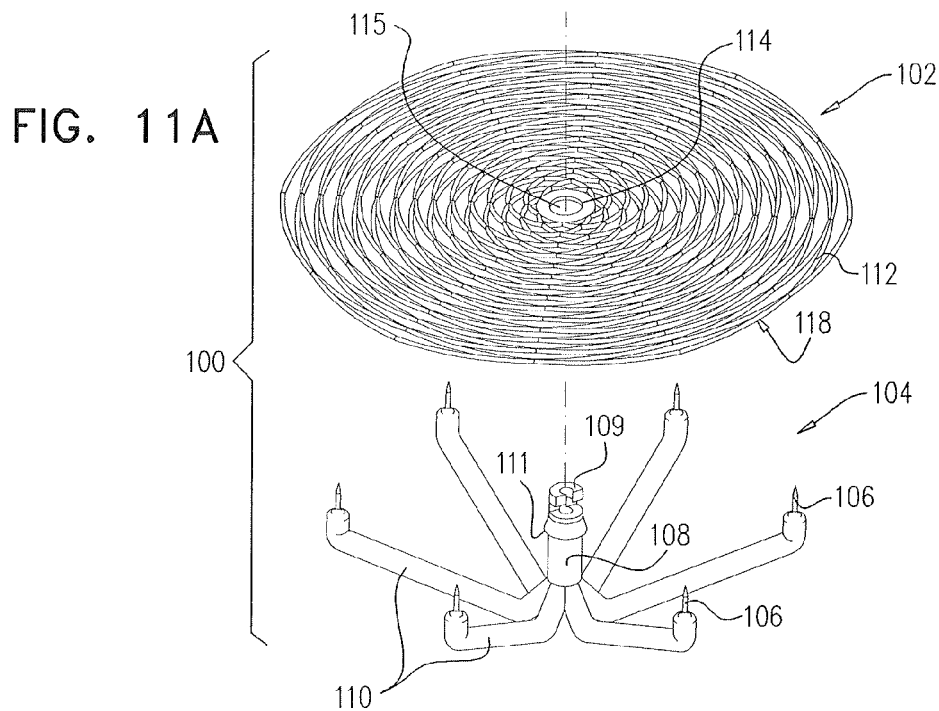
FIG. 11B
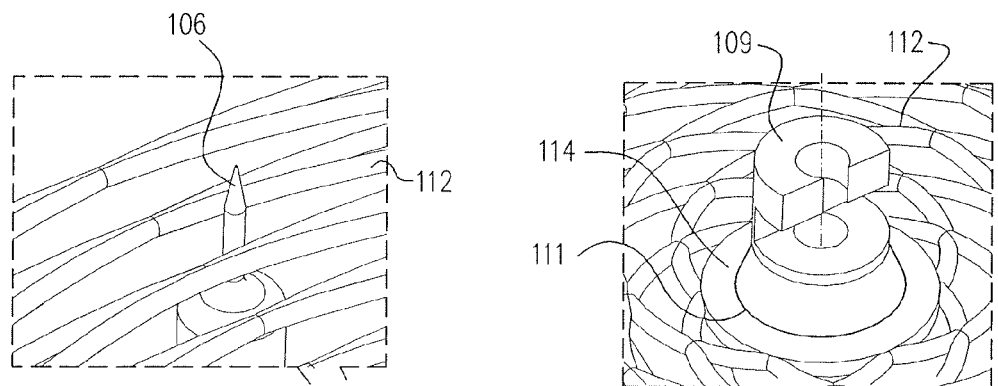
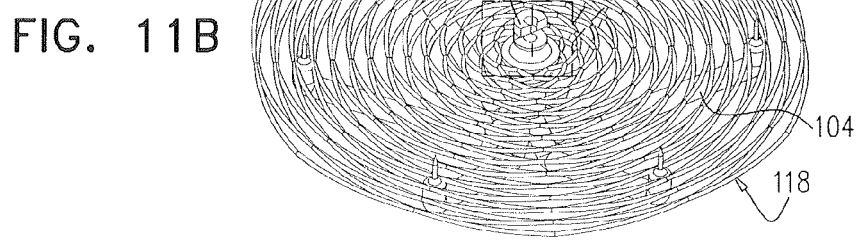

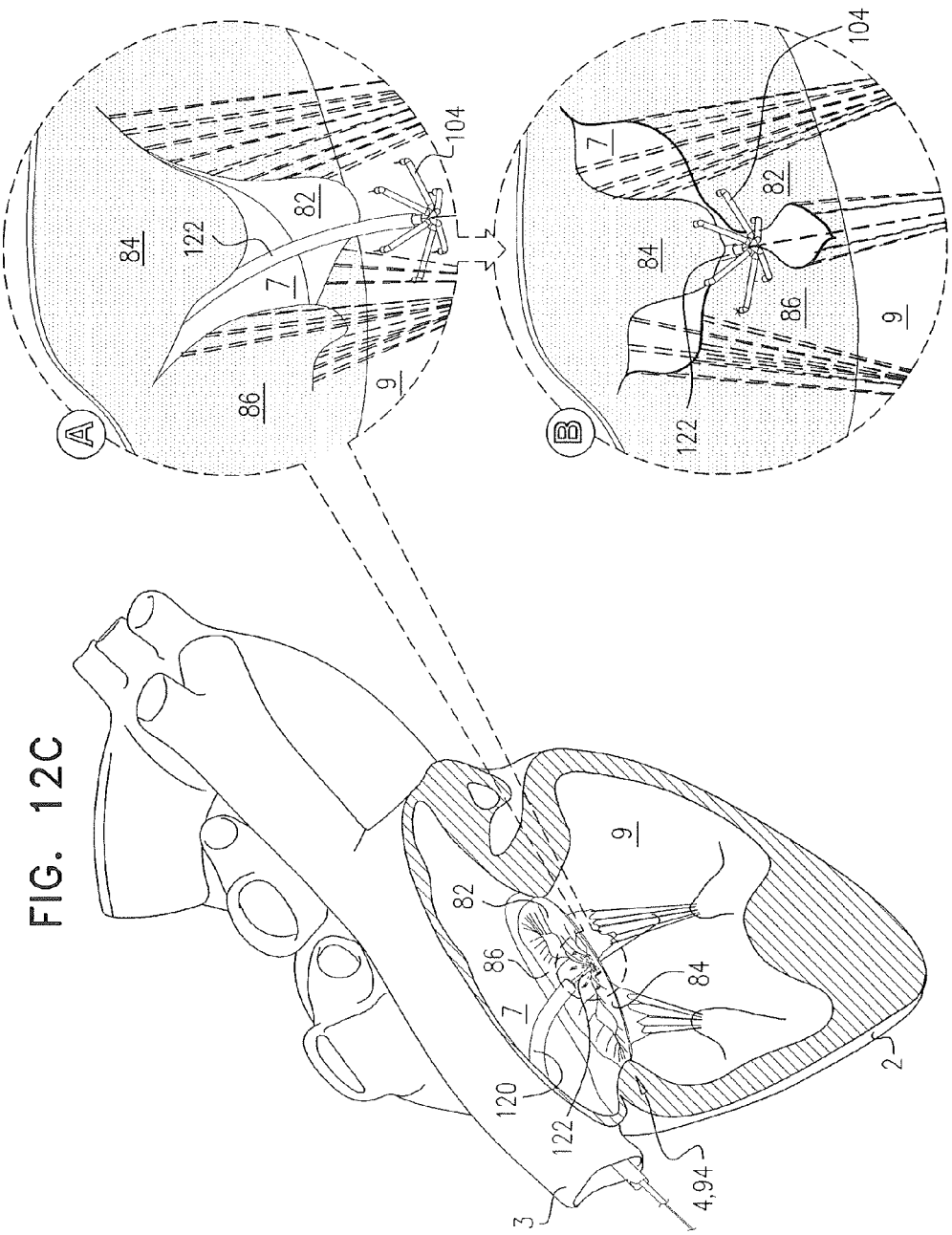

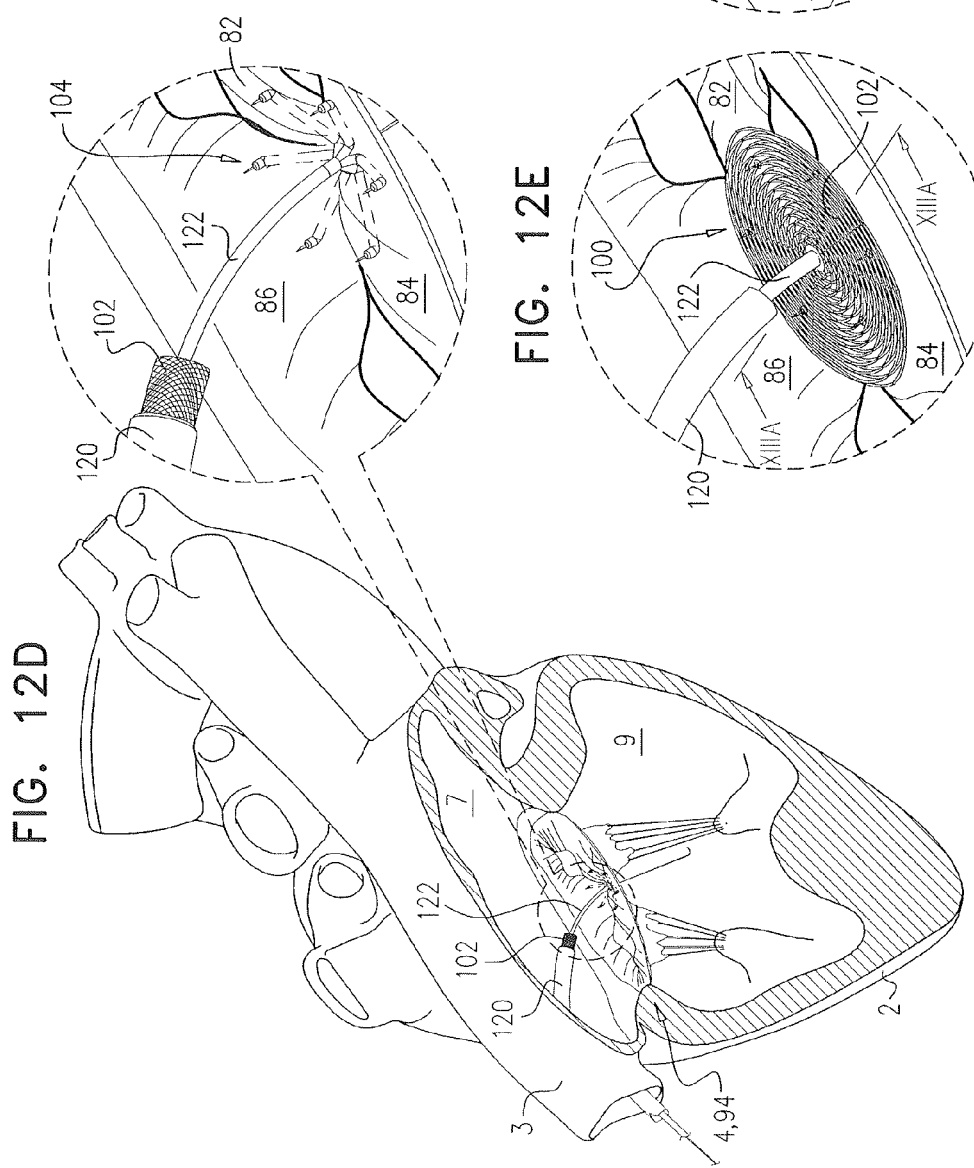

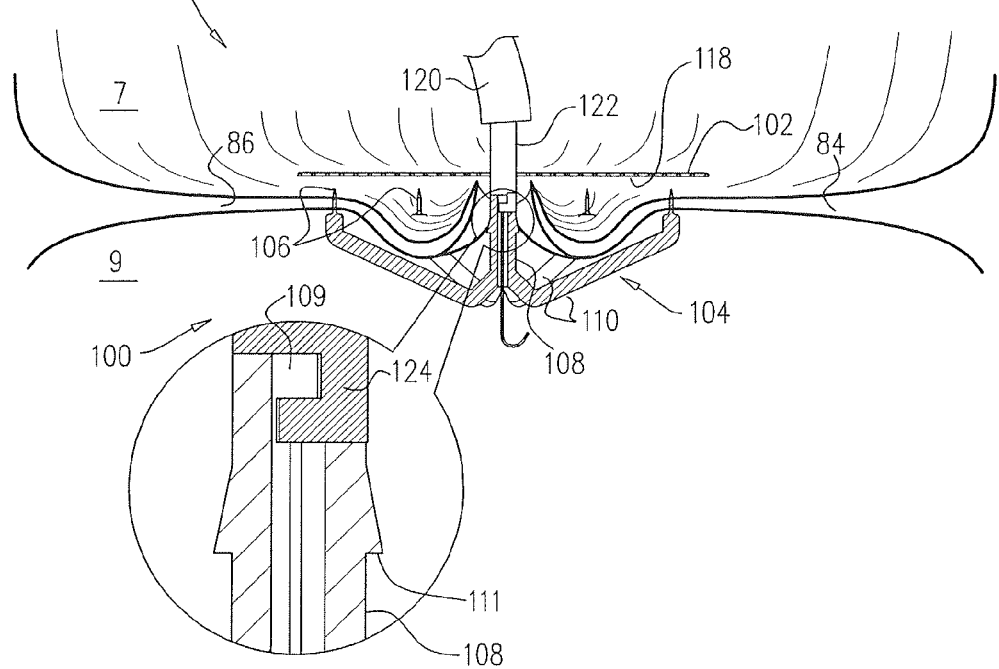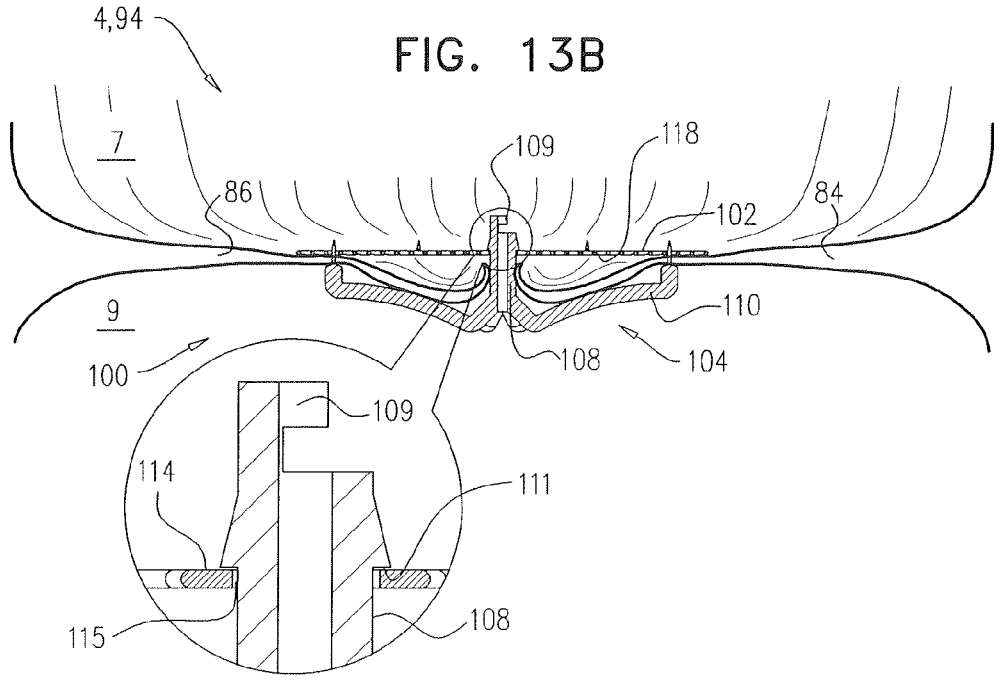

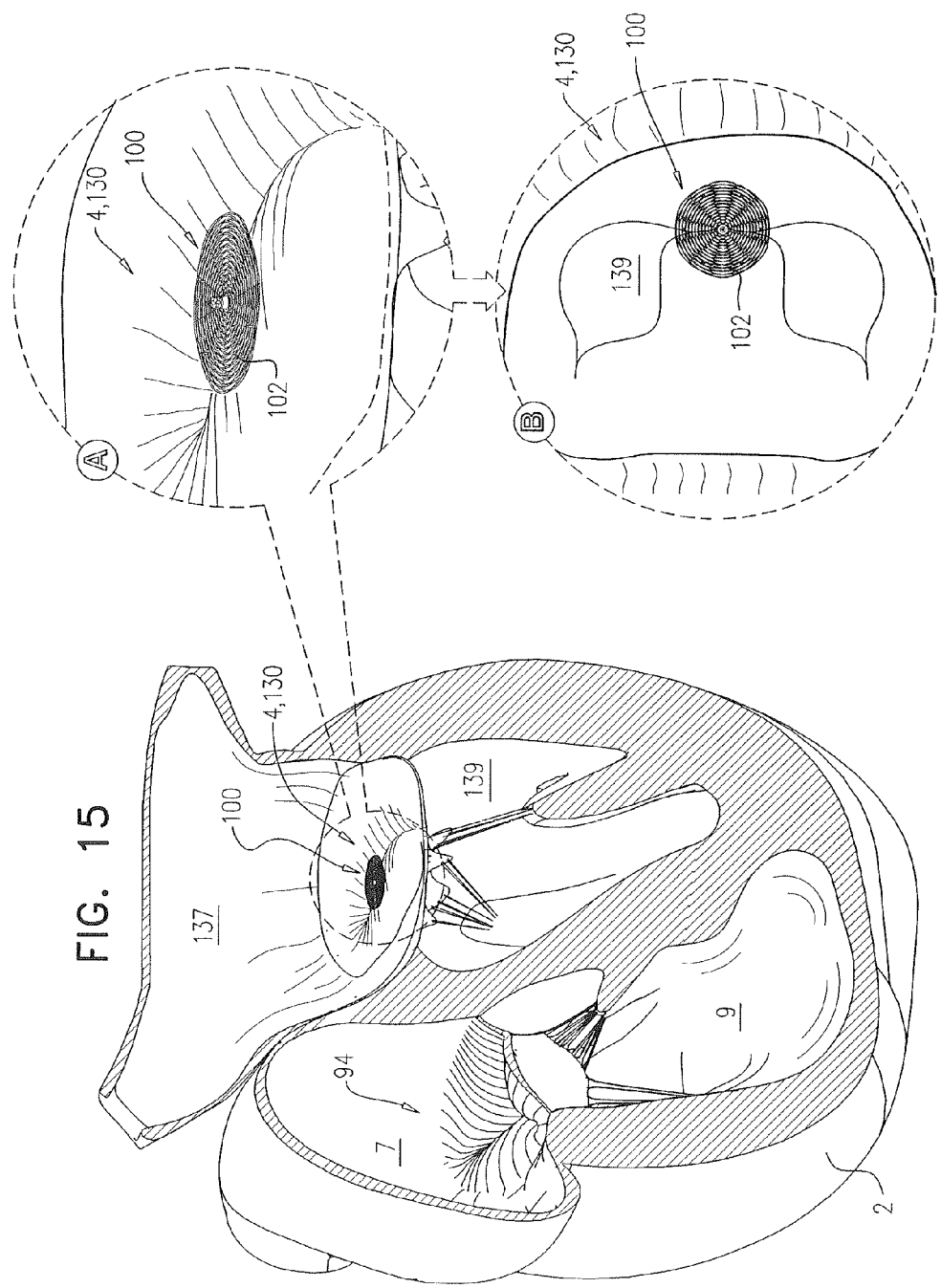

SUTURE-SECURING FOR CARDIAC VALVE REPAIR

CROSS-REFERENCE TO RELATED APPLICATIONS

The present application is a continuation of U.S. application Ser. No. 14/584,286, filed Dec. 29, 2014, now abandoned, which is a divisional of U.S. application Ser. No. 13/485,145, filed May 31, 2012, now U.S. Pat. No. 8,961,594.

FIELD OF THE INVENTION

Some applications of the present invention relate in general to surgical techniques. More specifically, some applications of the present invention relate to techniques for securing sutures. More specifically, some applications of the present invention relate to transluminal techniques for securing sutures.

BACKGROUND

Functional tricuspid regurgitation (FTR) is governed by several pathophysiologic abnormalities such as tricuspid valve annular dilatation, annular shape, pulmonary hypertension, left or right ventricle dysfunction, right ventricle geometry, and leaflet tethering. Treatment options for FTR are primarily surgical. The current prevalence of moderate-to-severe tricuspid regurgitation is estimated to be 1.6 million in the United States. Of these, only 8,000 patients undergo tricuspid valve surgeries annually, most of them in conjunction with left heart valve surgeries.

SUMMARY OF THE INVENTION

In some applications of the invention, apparatus and methods are provided for fixedly coupling sutures to each other. For some such applications, the apparatus comprises a suture-securing device that comprises two tubular elements that are movably coupled to each other. For other such applications, the apparatus comprises a suture-securing device that comprises a casing and a core that are movably coupled to each other. Both suture-securing devices described have an unlocked configuration, in which sutures are generally slidable through the device, and a locking configuration, in which the sutures are generally not slidable through the device.

In some applications of the invention, the suture-securing devices are configured to be biased to moving toward the locking configuration thereof, and are retained in the unlocked configuration by a constraint. For such applications, the devices automatically move toward the locking configuration when the constraint is removed.

In some applications of the invention, techniques are provided for using the suture-securing device to repair a heart valve, by fixedly coupling together sutures that are coupled to different parts of the annulus of the valve.

In some applications of the invention, apparatus and methods are provided for repairing a heart valve by sandwiching valve leaflets between a support and a securing element, such that multiple orifices are formed between respective portions of the valve leaflets. Typically, the support is generally disc-shaped, and comprises a wire-mesh. Typically, the securing element comprises a plurality of arms, one end of each arm coupled to a central core, and the other end of each arm coupled to leaflet-piercing elements, which protrude through the valve leaflets and into the wire mesh of the support.

There is therefore provided, in accordance with an application of the present invention, apparatus for use with a heart valve of a patient, the heart valve including at least two leaflets, the apparatus including:

a support, having a leaflet-engaging side, configured to be placed against a first side of the heart valve in a position in which respective portions of the leaflet-engaging side of the support are disposed against respective regions of respective leaflets of the valve; and a plurality of leaflet-piercing elements, deliverable to a second side of the heart valve of the patient, and configured to couple the support to the heart valve by (1) piercing the leaflets of the heart valve from the second side of the heart valve to the first side of the heart valve, and (2) coupling to the support while the support is in the position on the first side of the heart valve.

In an application, the support is flat.

In an application, the support is disc-shaped.

In an application, the support has a delivery configuration in which the support is generally cylindrical, and a deployed configuration in which the support is generally flat.

In an application, the support includes a braided wire mesh.

In an application, the leaflet-piercing elements include straight spikes.

In an application, the leaflet-piercing elements include barbs.

In an application, the leaflet-piercing elements include hooks.

In an application, the leaflet-piercing elements are configured to couple to the support by being configured to protrude into the support.

In an application, the leaflet-piercing elements are configured to couple to the support by being configured to protrude through the support.

In an application, the support is transluminally deliverable to the first side of the heart valve of the patient.

In an application, the leaflet-piercing elements are transluminally deliverable to the second side of the heart valve independently of the support.

In an application, the apparatus further includes a securing element, including:

a core;

two or more arms, an inner end of each arm being coupled to the core, and the arms extending radially outward from the core; and the leaflet-piercing elements, coupled to respective outer ends of each arm.

In an application, the securing element is transluminally deliverable to the second side of the heart valve independently of the support.

In an application, the apparatus is configured such that the leaflet-engaging elements are configured to be coupled to the support by the securing element being configured to be coupled to the support.

In an application, the apparatus is configured such that coupling the leaflet-engaging elements to the support while the support is in the position on the first side of the heart valve, sandwiches the leaflets of the heart valve between the support and the securing element.

In an application, the core defines a coupling portion, configured to couple the core to the support.

In an application, the apparatus is configured such that the coupling of the core to the support facilitates the coupling of the leaflet-piercing elements to the support.

In an application, the support defines an inner perimeter that defines an opening through the support, and the coupling portion is configured to couple the core to the support, by being configured to secure at least part of the coupling portion within the opening.

In an application, the core is configured to extend between the leaflets of the heart valve, from the second side of the heart valve to the first side of the heart valve, such that the coupling portion is couplable to the support at the first side of the heart valve.

In an application, the securing element has a delivery configuration and a deployed configuration, and the outer end of the arms are closer to each other in the delivery configuration than in the deployed configuration.

In an application:
the securing element is disposable within a sheath, and is removable from the sheath,
the delivery configuration defines a constrained configuration, the sheath being configured to constrain the securing element in the constrained delivery configuration,
the deployed configuration defines an unconstrained configuration, and
the securing element is configured to automatically move from the delivery configuration to the deployed configuration when the securing element is removed from the sheath.

There is further provided, in accordance with an application of the present invention, a method for use with a heart valve of a patient, the heart valve including at least two leaflets, the method including:
delivering, to a first side of the heart valve, a support, having a leaflet-engaging side;
delivering, to a second side of the heart valve, a plurality of leaflet-piercing elements;
piercing the leaflets of the valve, from the second side to the first side of the valve, with the leaflet-piercing elements; and
coupling the support to the leaflets, such that respective portions of the leaflet-engaging side of the support are disposed against respective regions of respective leaflets, by coupling, at the first side of the valve, the leaflet-piercing elements to the support.

In an application, delivering the support includes delivering a flat support.

In an application, delivering the support includes delivering a disc-shaped support.

In an application, delivering the support includes delivering a support that includes a braided wire mesh.

In an application, delivering the support includes:
percutaneously delivering the support while the support is in a generally-cylindrical delivery configuration thereof, and
subsequently, deploying the support into a generally flat deployed configuration thereof.

In an application, coupling the leaflet-piercing elements to the support includes advancing the leaflet-piercing elements into the support.

In an application, coupling the leaflet-piercing elements to the support includes advancing the leaflet-piercing elements through the support.

In an application, delivering the leaflet-piercing elements includes delivering the leaflet-piercing elements independently of delivering the support.

In an application, delivering the leaflet-piercing elements includes delivering, to the second side of the valve, a securing element that includes (1) a core, (2) two or more arms, an inner end of each arm being coupled to the core, and the arms extending radially outward from the core, and (3) the leaflet-piercing elements, coupled to respective outer ends of each arm.

In an application, coupling the leaflet-piercing elements to the support includes coupling the securing element to the support.

In an application, coupling the securing element to the support includes sandwiching the leaflets between the securing element and the support.

In an application, coupling the securing element to the support includes coupling the core to the support, and coupling the core to the support facilitates coupling the leaflet-piercing elements to the support.

In an application, the core defines a coupling portion, and coupling the securing element to the support includes coupling the coupling portion of the core to the support.

In an application, coupling the coupling portion to the support facilitates the coupling of the leaflet-piercing elements to the support.

In an application, the support defines an inner perimeter that defines an opening through the support, and coupling the coupling portion of the core to the support includes securing at least part of the coupling portion within the opening.

In an application, coupling the coupling portion of the core to the support, includes coupling the coupling portion to the support at the first side of the heart valve.

In an application, coupling the coupling portion to the support includes moving at least part of the coupling portion, from the second side of the heart valve, between the leaflets of the heart valve, to the first side of the heart valve.

There is further provided, in accordance with an application of the present invention, apparatus for use with one or more sutures, the apparatus including:
a first tubular element, shaped to define a first lumen therethrough, and having a first end and a second end; and
a second tubular element, shaped to define a second lumen therethrough, and having a first end and a second end,
the apparatus having:
an unlocked configuration in which:
the first end of the second tubular element is disposed closer to the first end of the first tubular element than is the second end of the second tubular element, and
the sutures are disposable within and slidable through the first and second lumens, and
a locking configuration in which:
the second end of the second tubular element is disposed closer to the first end of the first tubular element than is the first end of the second tubular element, and
the sutures are inhibited from sliding through the first and second lumens.

In an application, the second tubular element has a length, from the first end of the second tubular element to the second end of the second tubular element, that is smaller than the cross-sectional diameter of the first lumen.

In an application, the sutures include a first suture and a second suture, and the apparatus having a locking configuration in which the sutures are inhibited from sliding through the first and second lumens, includes the apparatus having a locking configuration in which the first suture is inhibited from moving with respect to the second suture.

In an application, the apparatus is configured such that:
in the unlocked configuration, the second end of the second tubular element is disposed outside of the first lumen, and in the locking configuration, the second end of the second tubular element is disposed within the first lumen.

In an application, the second end of the first tubular element is coupled to the first end of the second tubular element.

In an application, the apparatus is configured such that, when the sutures are disposed within the lumens of the first and second tubular elements, movement of the apparatus from the unlocked to the locking configuration rotates at least a portion of each suture.

In an application, the apparatus is configured such that movement of the apparatus from the unlocked to the locking configuration rotates the second tubular element.

In an application, the first and second tubular elements include a continuous piece of material.

In an application, the first tubular element is shaped such that the first lumen has a cross-sectional diameter that is greater than a cross-sectional diameter of the second lumen.

In an application, the first tubular element is shaped such that the first lumen has a cross-sectional diameter that is more than 1.1 times greater than the cross-sectional diameter of the second lumen.

In an application, the first tubular element is shaped such that the first lumen has a cross-sectional diameter that is less than 1.5 times greater than the cross-sectional diameter of the second lumen.

In an application:
the unlocked configuration includes a constrained configuration, and the locking configuration includes an unconstrained configuration, and
the apparatus is configured to be retained in the constrained unlocked configuration by a constraining force, and to automatically move toward the unconstrained locking configuration when the constraining force is removed.

In an application, the apparatus further includes a constraint, configured to provide the constraining force.

In an application, the constraint includes a rod, disposable in the lumen of at least one of the tubular elements, configured to provide the constraining force by being disposed in the lumen, the constraining force being removable by removing the rod from the lumen.

In an application, the constraint includes a constraining sheath, configured to provide the constraining force by being disposed around at least one of the tubular members, the constraining force being removable by removing the sheath from the at least one of the tubular members.

In an application, the first and second tubular elements both define respective inner and outer surfaces, and, in the locking configuration, at least part of the outer surface of the second tubular element is disposed against at least part of the inner surface of the first tubular element.

In an application, the apparatus is configured such that, when the sutures are disposed within the lumens of the first and second tubular elements, movement of the apparatus from the unlocked to the locking configuration sandwiches at least a portion of each suture between the outer surface of the second tubular element and the inner surface of the first tubular element.

In an application, the apparatus includes at least one helical element.

In an application, at least in the unlocked configuration, the apparatus defines a continuous helix from the first end of the first tubular element to the second end of the second tubular element.

In an application, the first tubular element includes a first helical element and the second tubular element includes a second helical element.

In an application, the second end of the first tubular element is coupled to the first end of the second tubular element by a connecting portion.

In an application, the tubular elements and the connecting portion include a continuous piece of material.

There is further provided, in accordance with an application of the present invention, apparatus for use with one or more sutures, the apparatus including:
a first tubular element, shaped to define a first lumen therethrough, and having a proximal end and a distal end; and
a second tubular element, shaped to define a second lumen therethrough, and having a first end and a second end, the apparatus having:
an unlocked configuration in which:
the second end of the second tubular element is disposed distally to the first end of the second tubular element, and
the sutures are disposable within and slidable through the first and second lumens, and
a locking configuration in which:
the first end of the second tubular element is disposed distally to the second end of the second tubular element, and
the sutures are inhibited from sliding through the first and second lumens.

In an application, the apparatus is configured such that:
in the unlocked configuration, the second end of the second tubular element is disposed outside of the first lumen, and
in the locking configuration, the second end of the second tubular element is disposed within the first lumen.

In an application, the apparatus is configured such that, when the sutures are disposed within the lumens of the first and second tubular elements, movement of the apparatus from the unlocked to the locking configuration rotates at least a portion of each suture.

In an application, the first and second tubular elements both define respective inner and outer surfaces, and, in the locking configuration, at least part of the outer surface of the second tubular element is disposed against at least part of the inner surface of the first tubular element.

In an application, the apparatus is configured such that, when the sutures are disposed within the lumens of the first and second tubular elements, movement of the apparatus from the unlocked to the locking configuration sandwiches at least a portion of each suture between the outer surface of the second tubular element and the inner surface of the first tubular element.

There is further provided, in accordance with an application of the present invention, apparatus for use with one or more sutures, the apparatus including:
a first tubular element, shaped to define a first lumen therethrough; and
a second tubular element, coupled to the first tubular element, and shaped to define a second lumen therethrough,
the apparatus having:
an unlocked configuration in which at least a quarter of the second tubular element is disposed outside of the first lumen, and the sutures are disposable within and slidable through the first and second lumens, and
a locking configuration in which at least a quarter of the second tubular element is disposed inside the first lumen, and the sutures are inhibited from sliding through the first and second lumens, and
the apparatus being constrainable in the unlocked configuration by a removable constraining force, and configured to automatically move toward the second configuration when the constraining force is removed.

In an application, the apparatus is configured such that, when the sutures are disposed within the lumens of the first and second tubular elements, movement of the apparatus from the unlocked to the locking configuration rotates at least a portion of each suture.

In an application, the first and second tubular elements both define respective inner and outer surfaces, and, in the locking configuration, at least part of the outer surface of the second tubular element is disposed against at least part of the inner surface of the first tubular element.

In an application, the apparatus is configured such that, when the sutures are disposed within the lumens of the first and second tubular elements, movement of the apparatus from the unlocked to the locking configuration sandwiches at least a portion of each suture between the outer surface of the second tubular element and the inner surface of the first tubular element.

There is further provided, in accordance with an application of the present invention, apparatus for use with one or more sutures, the apparatus including:

a first tubular element, shaped to define a first lumen therethrough; and a second tubular element shaped to define a second lumen therethrough, the second tubular element being coupled to the first tubular element at a coupling point, the coupling point being configured to facilitate deflection of the second tubular element around the coupling point, and the apparatus:

having an unlocked configuration in which the sutures are disposable within and slidable though the first and second lumens, and a locking configuration in which the sutures are inhibited from sliding through the first and second lumens, being configured to be constrainable in the unlocked configuration by a constraining force, and being configured, when the constraining force is removed, to automatically move from the unlocked configuration to the locking configuration, by the second tubular element deflecting around the coupling point.

In an application, the apparatus is configured such that, when the sutures are disposed within the lumens of the first and second tubular elements, the deflecting of the second tubular element around the coupling point rotates at least a portion of each suture.

In an application, the first and second tubular elements both define respective inner and outer surfaces, and, in the locking configuration, at least part of the outer surface of the second tubular element is disposed against at least part of the inner surface of the first tubular element.

In an application, the apparatus is configured such that, when the sutures are disposed within the lumens of the first and second tubular elements, the deflecting of the second tubular element around the coupling point sandwiches at least a portion of each suture between the outer surface of the second tubular element and the inner surface of the first tubular element.

There is further provided, in accordance with an application of the present invention, apparatus for use with one or more sutures, the apparatus including:

a casing, shaped to define a cavity, and one or more openings in which the sutures are disposable;

a core, disposed in the cavity, and shaped to define a lumen in which the sutures are disposable, the apparatus:

having an unlocked configuration in which the sutures are disposable within and slidable through the openings and the lumen, and a locking configuration in which the sutures are inhibited from sliding through the openings and the lumen, being movable from the unlocked configuration to the locking configuration, and being configured such that, when the sutures are disposed within the openings and the lumen, and the apparatus moves from the unlocked configuration to the locking configuration, the apparatus (1) cuts the sutures at a cutting site of the apparatus, and (2) becomes coupled to the sutures at a coupling site of the apparatus.

In an application:

the casing defines two or more openings, the openings being provided along a longitudinal axis of the casing, in the unlocked configuration of the apparatus, the lumen of the core is disposed along the axis, and between the openings, and in the locking configuration of the apparatus, the core is disposed with respect to the casing in a manner in which the lumen of the core is not disposed along the axis.

In an application:

the casing defines two or more openings, in the unlocked configuration of the apparatus, the lumen of the core is generally in fluid communication with the openings, and in the locking configuration of the apparatus, the lumen of the core is generally not in fluid communication with the openings.

In an application:

the unlocked configuration includes a constrained configuration, and the locking configuration includes an unconstrained configuration, and the apparatus is configured to be retained in the constrained unlocked configuration by a constraining force, and to automatically move toward the unconstrained locking configuration when the constraining force is removed.

In an application, the apparatus further includes a constraint, configured to provide the constraining force.

In an application, the constraint includes a constraining sheath.

In an application, the cutting site includes at least one cutting edge, and the apparatus is configured to cut the sutures by pushing the sutures against the cutting edge.

In an application:

the at least one cutting edge includes first and second cutting edges, the casing is shaped to define the first cutting edge, and the core is shaped to define the second cutting edge. 83. A method for use with one or more sutures at an anatomical site of a patient, the method including:

delivering, to a vicinity of the anatomical site, apparatus that includes (1) a first tubular element, shaped to define a first lumen therethrough, and having a first end and a second end, and (2) a second tubular element, shaped to define a second lumen therethrough, and having a first end and a second end;

sliding the apparatus over at least part of the sutures while the apparatus is in an unlocked configuration thereof in which (1) the first end of the second tubular element is disposed closer to the first end of the first tubular element than is the second end of the second tubular element, and (2) the sutures are slidable through the first and second lumens; and securing the apparatus to the sutures by moving the apparatus into a locking configuration thereof in which: (1)

the second end of the second tubular element is disposed closer to the first end of the first tubular element than is the first end of the second tubular element, and (2) the sutures are inhibited from sliding through the first and second lumens.

There is further provided, in accordance with an application of the present invention, a method for use with one or more sutures at an anatomical site of a patient, the method including:

delivering, to a vicinity of the anatomical site, apparatus that includes (1) a first tubular element, shaped to define a first lumen therethrough, and having a first end and a second end, and (2) a second tubular element, shaped to define a second lumen therethrough, and having a first end and a second end;

sliding the apparatus over at least part of the sutures while the apparatus is in an unlocked configuration thereof in which (1) the first end of the second tubular element is disposed closer to the first end of the first tubular element than is the second end of the second tubular element, and (2) the sutures are slidable through the first and second lumens;

and subsequently inhibiting the sutures from sliding through the first and second lumens by moving the apparatus into a locking configuration in which the second end of the second tubular element is disposed closer to the first end of the first tubular element than is the first end of the second tubular element.

In an application, in the unlocked configuration, the second end of the second tubular element of the apparatus is disposed outside of the first lumen, and moving the apparatus into the locking configuration includes moving the second end of the second tubular element into the first lumen.

In an application, moving the apparatus into the locking configuration includes moving at least a quarter of the second tubular element into the first lumen.

In an application, moving the apparatus into the locking configuration includes sandwiching at least a portion of each suture between an outer surface of the second tubular element and an inner surface of the first tubular element.

In an application, the apparatus is configured to be constrained in the unlocked configuration by a constraining force, and moving the apparatus into the locking configuration includes removing the constraining force.

In an application, removing the constraining force includes removing, from the lumen of at least one of the tubular elements, a rod that is (1) disposed in the lumen of the least one of the tubular elements, and (2) configured to provide the constraining force.

In an application, removing the constraining force includes removing, from around at least one of the tubular elements, a constraining sheath that is (1) disposed around the at least one of the tubular elements, and (2) configured to provide the constraining force.

In an application, moving the apparatus into the locking configuration includes rotating the second tubular element.

In an application, the first tubular element is coupled to the second tubular element via a coupling point, and rotating the second tubular element includes deflecting the second tubular element around the coupling point.

There is further provided, in accordance with an application of the present invention, a method for use with one or more sutures at an anatomical site of a patient, the method including:

delivering, to a vicinity of the anatomical site, apparatus that includes (1) a casing, shaped to define a cavity, and one or more openings in which the sutures are disposable, and (2) a core, disposed in the cavity, and shaped to define a lumen in which the sutures are disposable;

sliding the apparatus over at least part of the sutures while the apparatus is in an unlocked configuration thereof, in which the sutures are slidable through the openings and the lumen; and subsequently, by moving the apparatus into a locking configuration thereof, simultaneously (1) inhibiting the sutures from sliding through the lumen by coupling the apparatus to the sutures at a coupling site of the apparatus, and (2) cutting the sutures with one or more cutting edges at a cutting site of the apparatus.

In an application, the apparatus is configured to be constrained in the unlocked configuration by a constraining force, and moving the apparatus into the locking configuration includes removing the constraining force.

In an application, removing the constraining force includes removing, from around at least part of the core, a constraining sheath that is (1) disposed around the at least part of the core, and (2) configured to provide the constraining force.

For some applications, techniques described herein are practiced in combination with techniques described in one or more of the references cited in the Background section and Cross-references section of the present patent application.

BRIEF DESCRIPTION OF THE DRAWINGS

FIGS. 3-7 are schematic illustrations of steps in the use of the apparatus of FIGS. 1A-B and 2A-B to repair a cardiac valve, in accordance with some applications of the invention;

FIGS. 8A-B and 9A-B are schematic illustrations of a suture-securing device, in accordance with some applications of the invention;

FIG. 10 is a schematic illustration of the suture-securing device of FIGS. 8A-B and 9A-B, having been used to repair a cardiac valve, in accordance with some applications of the invention;

FIGS. 11A-B are schematic illustrations of apparatus for repairing a heart valve, in accordance with some applications of the invention;

FIGS. 12A-F, 13A-B and 14 are schematic illustrations of the use of the apparatus of FIGS. 11A-B to repair a heart valve, in accordance with some applications of the invention; and FIG. 15 is a schematic illustration of the apparatus of FIGS. 11A-B having been used to repair a heart valve, in accordance with some applications of the invention.

DETAILED DESCRIPTION OF EMBODIMENTS

Reference is made to FIGS. 1A-B and 2A-B, which are schematic illustrations of apparatus 20, comprising a suture-securing device 22, in accordance with some applications of the invention. Device 22 has an unlocked configuration in which one or more sutures are generally slidable through the device, and a locking configuration in which the sutures are generally not slidable through the device, and is movable from the unlocked configuration to the locking configuration.

Figure 1A:
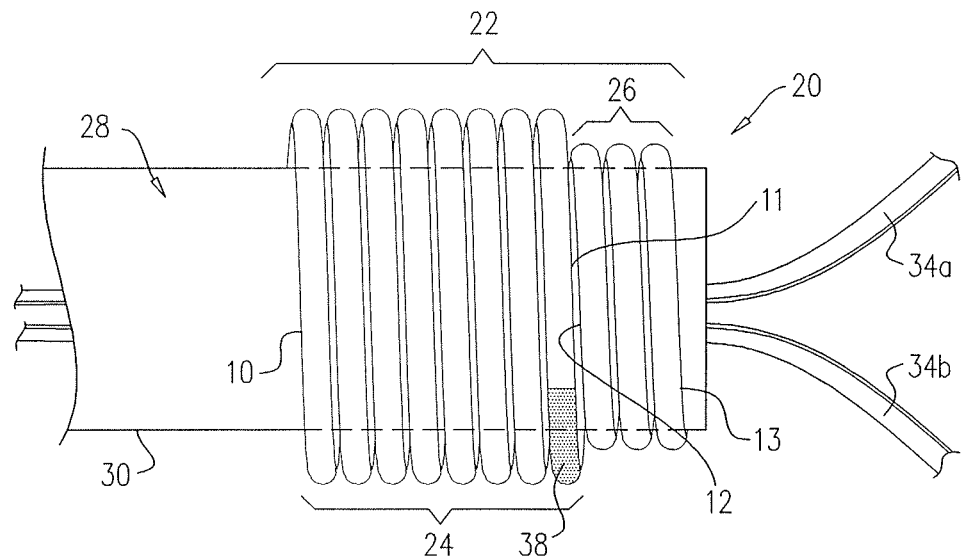
FIGS. 1A-B and 2A-B are schematic illustrations of apparatus comprising a suture-securing device, in accordance with some applications of the invention.
Figure 1B:
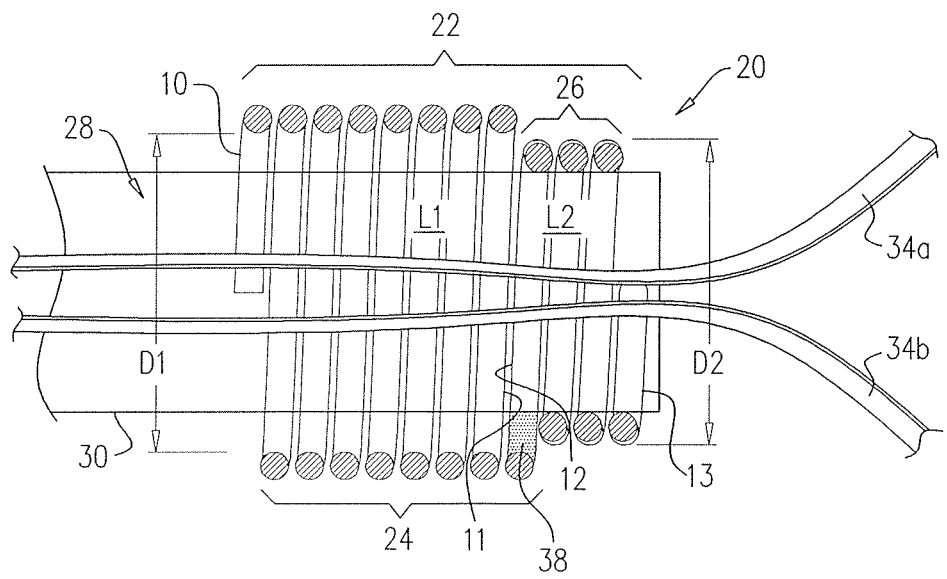

FIGS. 1A-B show device 22 in the unlocked configuration thereof. FIG. 1A shows a side view of device 22 being used with two sutures 34*a* and 34*b*, and FIG. 1B shows a cutaway view of the same. It is to be noted that, although device 22 is shown being used with two individual sutures, the device may be used with two portions of the same suture (e.g., the suture is looped), and/or with more or fewer sutures (e.g., to secure the device and/or an element coupled thereto, to a particular point on a single suture). It is to be further noted that, although sutures 34*a* and 34*b* are shown as ribbon-like sutures (e.g., having a generally rectangular cross-section), any suitable type of suture, as is known in the art, may be used.

Device 22 comprises a first tubular element 24, which is shaped to define a first lumen L1, a first end 10 and a second end 11, and a second tubular element 26, which is shaped to define a second lumen, a first end 12 and a second end 13. Typically, second tubular element 26 is narrower than first tubular element 24. That is, lumen L2 typically has a smaller transverse cross-sectional area than does lumen L1. Typically, the second tubular element has an outer edge that has a diameter D2 that is smaller than a diameter D1 of an inner edge of the first tubular element.

For some applications of the invention, diameter D1 is more than 1.1 times greater and/or less than 1.5 times greater than diameter D2. Typically, second tubular element 26 has a longitudinal length (i.e., from first end 12 to second end 13) that is smaller than diameter D1 of first tubular element 24, e.g., so as to facilitate rotation of the second tubular element within lumen L1 of the first tubular element.

Typically, device 22 is used in catheter-based procedures or minimally-invasive procedures, and is positioned with respect to the operating physician such that second tubular element 26 is distal to first tubular element 24. Alternatively, the device is positioned with respect to the physician such that the first tubular element is distal to the second tubular element. For some applications, device 22 may be used in a surgical procedure, e.g., an open-heart procedure.

In the unlocked configuration of device 22, the first and second tubular elements are typically disposed end to end. That is, in the unlocked configuration of device 22, one or more of the following are typically true:

(1) first end 12 of the second tubular element is disposed closer to first end 10 of the first tubular element than is second end 13 of the second tubular element, (2) second end 13 of the second tubular element is disposed distally (i.e., with respect to the operating physician) to first end 12 of the second tubular element, and (3) at least a quarter (e.g., all) of second tubular element 26 is disposed outside of lumen L1 of the first tubular element.

In the unlocked configuration, sutures 34*a* and 34*b* are slidable through device 22, i.e., through lumens L1 and L2 of tubular elements 24 and 26. That is, in the unlocked configuration, the device is slidably coupled to the sutures, i.e., is slidable over the sutures. Typically, device 22 is delivered to an anatomical site (e.g., in a vicinity of a site being treated) with sutures 34*a* and 34*b* pre-threaded through the device.

Typically, and as shown in FIGS. 1A-B, device 22 comprises at least one helical element, e.g., a coil. For example, and as shown in FIGS. 1A-B, tubular elements 24 and 26 may be defined by at least one helix. Further typically, device 22 comprises a continuous piece of material. For example, device 22 may be fabricated from a single elongate piece of material, such as a wire, that has been shaped to define tubular elements 24 and 26 (e.g., by being shaped to define a first helix that defines tubular element 24, and a second helix that defines tubular element 26). Typically, the material comprises a metal such as, but not limited to, stainless steel, titanium, nickel titanium (Nitinol), nickel cobalt, and/or cobalt chrome. For some applications, the material comprises a polymer and/or a resin. Further typically, and as described hereinbelow with reference to FIGS. 2A-B, the material comprises a shape-memory material.

Helical elements 24 and 26 are typically coupled by a connecting portion 38, which facilitates movement of device 22 from the unlocked configuration to the locking configuration. For some applications in which tubular elements 24 and 26 are defined by helices and comprise a single piece of material, connecting portion 38 also comprises the single piece of material. That is, for such applications, device 22, comprising connecting portion 38, comprises a single piece of material.

Figure 2A:
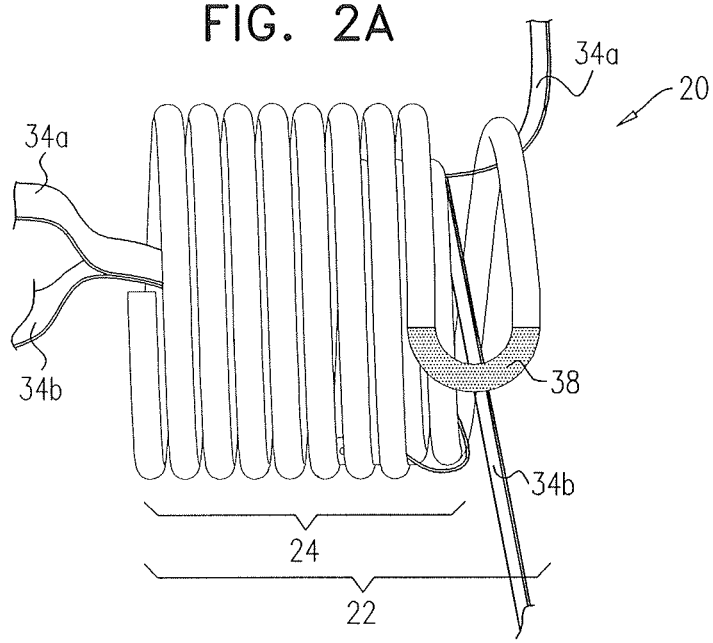
Figure 2B:
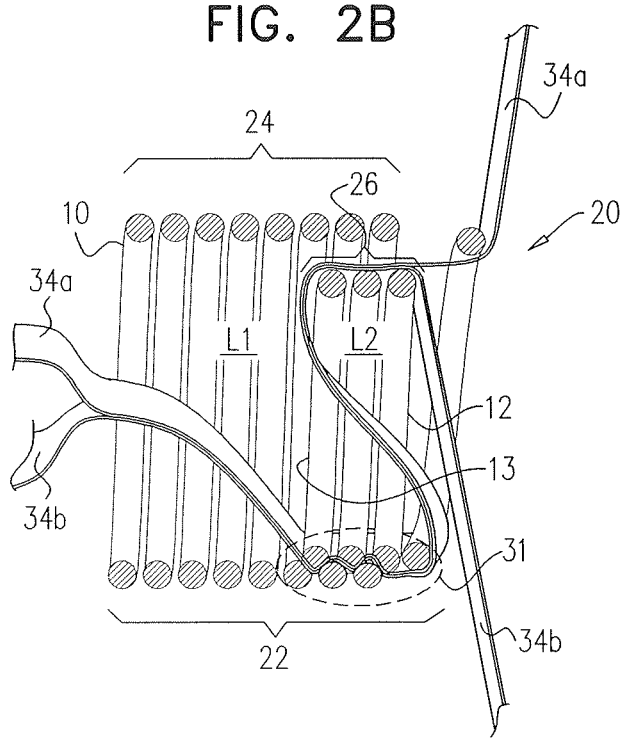

FIGS. 2A-B show device 22 in the locking configuration thereof, i.e., after having moved into the locking configuration. FIG. 2A shows a side view of device 22 being used with two sutures 34*a* and 34*b*, and FIG. 2B shows a cutaway view of the same. In the locking configuration of device 22, second tubular element 26 is oriented at about 180 degrees compared to its position in the unlocked configuration of the device. That is, when device 22 moved from the unlocked to the locking configuration, the second tubular element rotates and/or is deflected around an axis that is generally orthogonal to a longitudinal axis from first end 10 of the first tubular element to second end 13 of the second tubular element. Typically, and as shown in FIGS. 2A-B, second tubular element 26 is deflected around connecting portion 38.

Typically, in the locking configuration of device 22, one or more of the following are true:

(1) second end 13 of the second tubular element is disposed closer to first end 10 of the first tubular element than is first end 12 of the second tubular element, (2) first end 12 of the second tubular element is disposed distally (i.e., with respect to the operating physician) to second end 13 of the second tubular element, and (3) at least a quarter of second tubular element 26 is disposed inside lumen L1 of the first tubular element.

In the locking configuration, sutures 34*a* and 34*b* are generally not slidable through device 22, i.e., through lumens L1 and L2 of tubular elements 24 and 26. That is, in the locking configuration, the device is fixedly coupled to the sutures, i.e., is generally not slidable over the sutures. Typically, the device is fixedly coupled to the sutures by sandwiching at least part of the sutures between the two tubular elements, e.g., between the outer edge of second tubular element 26 and the inner edge first tubular element 24, as shown at coupling zone 31 in FIG. 2B.

As described hereinabove, device 22 (i.e., the tubular elements and coupling portion thereof) typically comprises a single piece of material that has been fabricated into at least one helix. Typically, device 22 comprises a shape-memory material, which is configured to be biased (e.g., is shape-set) such that the device moves toward the locking configuration thereof. For such applications, the device is retained in the unlocked configuration by at least one constraint 28 (see FIGS. 1A-B), which provides a constraining force. That is, the locking configuration is an unconstrained locking configuration, and the unlocked configuration is a constrained unlocked configuration.

For some applications, and as shown in FIGS. 1A-B, the constraint comprises a rod 30, and the constraining force is provided by the distal end of the rod being disposed in lumen L2 of second tubular element 26. So as to move device 22 into the locking configuration (e.g., so as to fixedly couple the device to the sutures), the surgeon removes the constraining force, e.g., by removing the constraint, such as by withdrawing rod 30 from at least lumen L2, such that the device automatically moves to the locking configuration.

For applications of the invention in which device 22 is constrained in the unlocked configuration by rod 30, rod 30 is typically shaped to define a lumen, and the sutures are slidable through the device by being slidable through the lumen of the rod.

For some applications, device 22 is constrained in the unlocked configuration by a constraining sheath (not shown) for delivery to an intracorporeal site. At, or in the vicinity of, the intracorporeal site, the device is exposed from the delivery sheath and automatically moves into the locking configuration.

Reference is made to FIGS. 3-7, which are schematic illustrations showing the use of apparatus 20 to treat a condition (e.g., regurgitation or leaflet prolapse) of a cardiac valve 4 of a heart 2 of a patient, in accordance with some applications of the invention. FIGS. 3-7 show valve 4, comprising a tricuspid valve 94, being treated via an inferior vena cava 3 of the patient (e.g., transfemorally). However, the scope of the invention includes the treatment of other heart valves and the use of other access routes, mutatis mutandis. In brief (1) distal ends of sutures 34a and 34b are coupled to two sites on annulus 5 of valve 4, (2) the sutures are placed under tension with respect to each other so as to draw the sites on the annulus toward each other, (3) apparatus is used to secure the sutures in the under-tension configuration, and (4) the sutures are cut and released, so as to leave the sutures under tension and the valve in the drawn-together configuration.

FIG. 3 shows a catheter 46 having been advanced through the inferior vena cava and into the right atrium 7 of the heart of the patient. Via catheter 46, a first helical anchor 40a, coupled to a distal end of suture 34a is coupled to (i.e., screwed into) a first site 6 on annulus 5. Typically, anchor 40a is delivered via a first inner sheath 44a.

Subsequently, and as shown in FIG. 4, a second helical anchor 40b, coupled to a distal end of suture 34b is coupled to a second site 8 on annulus 5. Typically, second site 8 is at least 1 cm from first site 6, such as a quarter of the way around annulus 5 from the first site, such as on the opposite side of the annulus to the first site.

For some applications in which cardiac valve 4 comprises tricuspid valve 94, first site 6 is typically in a vicinity of an anterior-posterior commissure (APC) 88 (i.e., the commissure between anterior leaflet 82 and posterior leaflet 84) of the valve, and second site 8 is in a vicinity of the septal leaflet of the valve.

Typically, anchor 40b is delivered via a second inner sheath 44b. Alternatively, anchors 40a and 40b are delivered via the same inner sheath.

Figure 5:
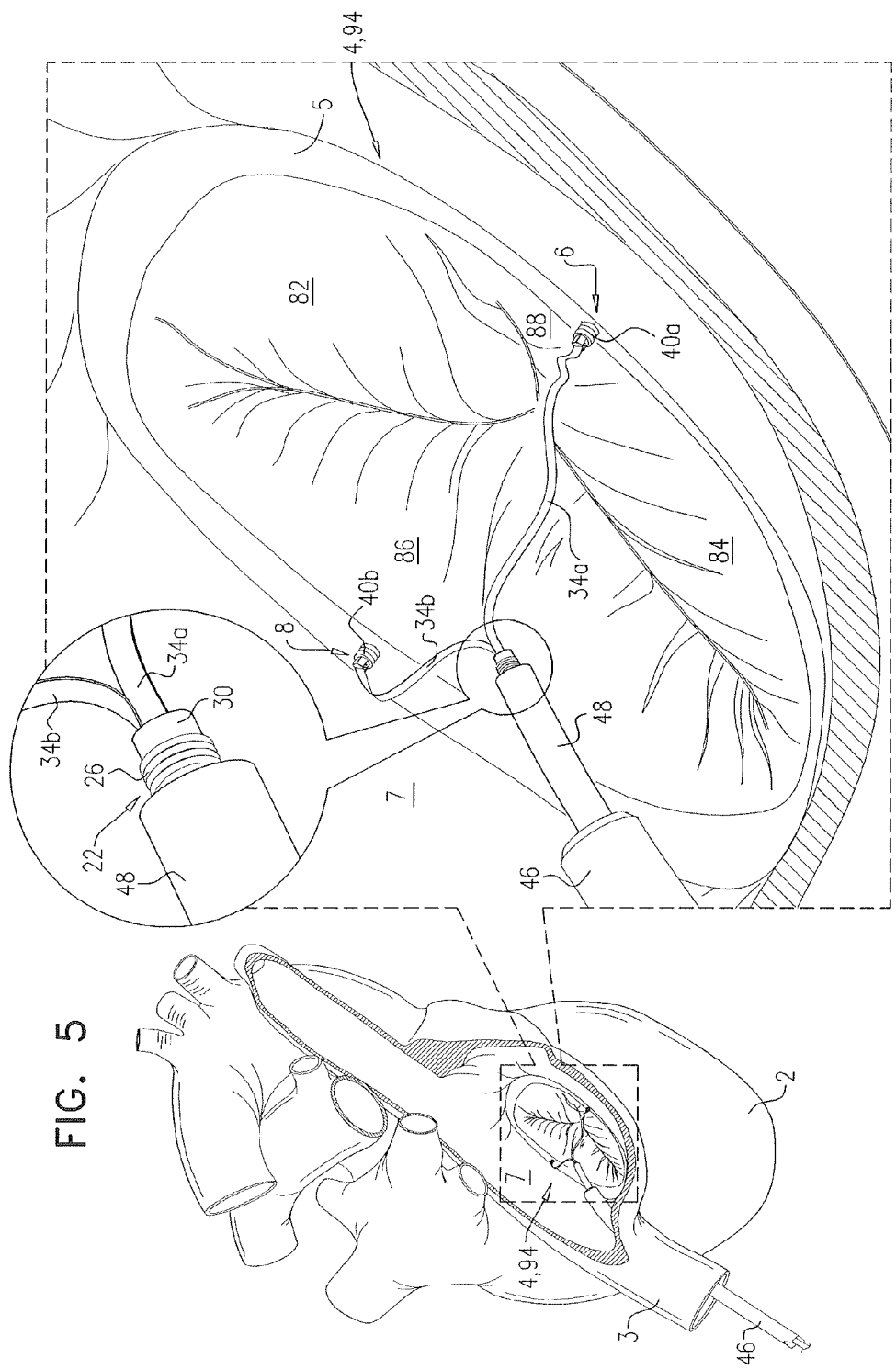

FIG. 5 shows apparatus 20, comprising suture-securing device 22, having been advanced through catheter 46. For some applications, and as shown in FIG. 5, device 22 is delivered via an outer sheath 48. Device 22 is typically delivered in the unlocked configuration thereof, and is typically constrained in the unlocked configuration by rod 30, as described hereinabove. Rod 30 and device 22 are slid over at least part of sutures 34a and 34b. For example, the sutures and helical anchors may be delivered via the lumen of rod 30 (e.g., inner sheaths 44a and 44b may be advanced through the lumen of rod 30).

Figure 6:
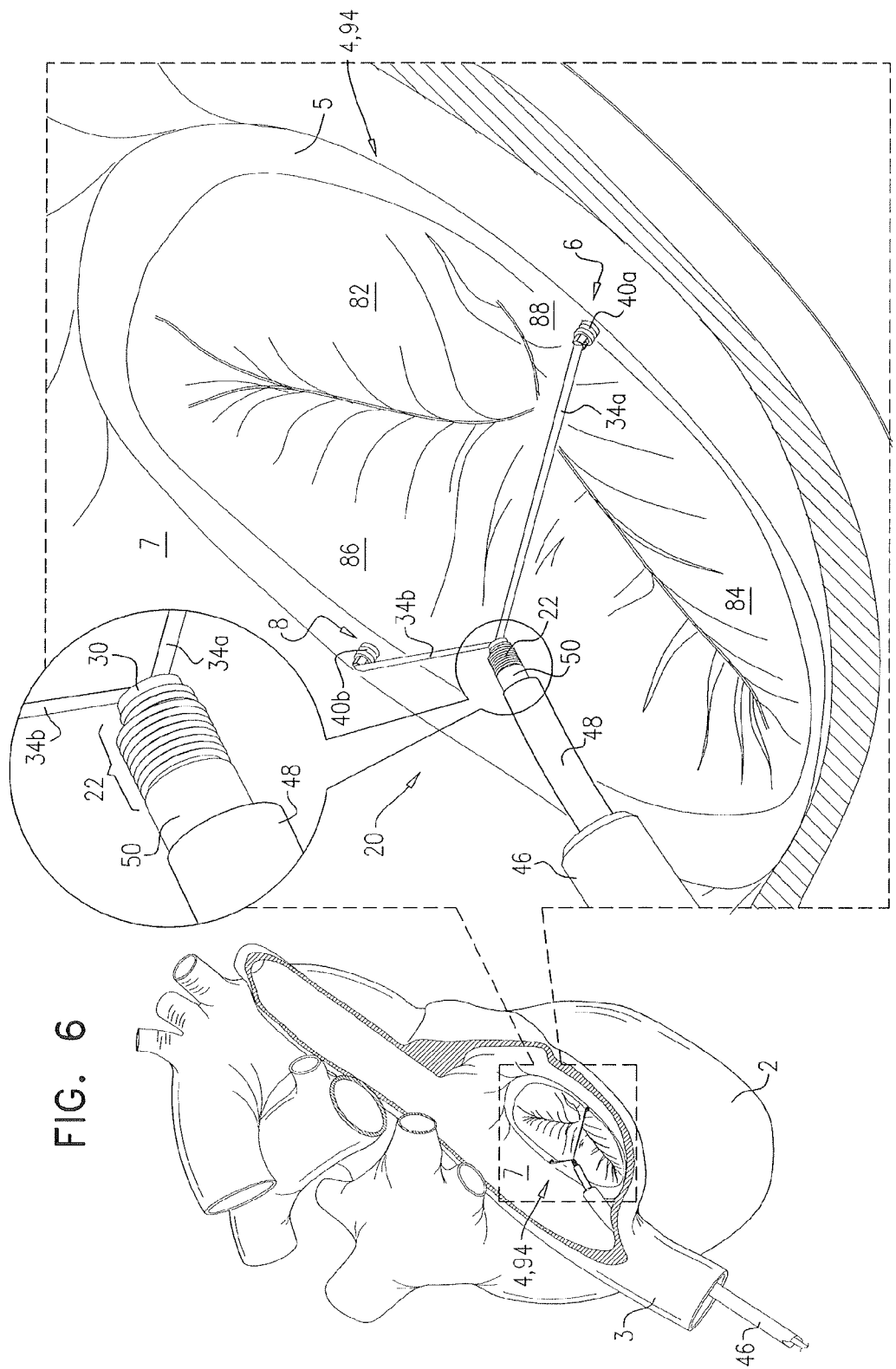

FIG. 6 shows sutures 34a and 34b having been placed under tension at least with respect to each other, e.g., by pulling respective proximal ends of the sutures proximally and/or by pushing device 22 distally, such as by using a controller 50. The tension draws together anchors 40a and 40b, and thereby draws together sites 6 and 8. Thereby, the annulus of valve 4 is reshaped, so as to treat valve prolapse. This reshaping is typically monitored in real-time (e.g., using ultrasound techniques) so that the operating physician may determine when acceptable reshaping has been achieved.

Reference is now made to FIG. 7. Once the operating physician determines that acceptable reshaping has been achieved, device 22 is moved into the locking configuration, e.g., by withdrawing rod 30 proximally. Typically, sutures 34a and 34b are subsequently released, e.g., by being cut at a proximal side of device 22. Rod 30 and the sheaths and catheter are subsequently removed from the body of the patient.

Reference is made to FIGS. 8A-B and 9A-B, which are schematic illustrations of a suture-securing device 60, in accordance with some applications of the invention. Device 60 has an unlocked configuration in which one or more sutures are generally slidable through the device, and a locking configuration in which the sutures are generally not slidable through the device, and is movable from the unlocked configuration to the locking configuration.

FIGS. 8A-B show device 60 in the unlocked configuration thereof. FIG. 8A shows a perspective view of device 60 being used with two sutures 34a and 34b, and FIG. 8B shows a cutaway view of the same. FIG. 8A further shows an exploded view of device 60. It is to be noted that, although device 60 is shown being used with two individual sutures, the device may be used with two portions of the same suture (e.g., the suture is looped), and/or with more or fewer sutures (e.g., to secure the device and/or an element coupled thereto, to a particular point on a single suture).

Device 60 comprises a casing 62, shaped to define a cavity 63 and one or more openings 64, and a core 66, disposed in cavity 63, and shaped to define a lumen L3 therethrough. Typically, casing 62 defines two openings 64. Typically, cavity 63 is open at a lateral side of the casing. Core 66 is movable, at least in part, within cavity 63. Typically, a pin 70 is disposed through casing 62 and core 66, such that core 66 is movable within cavity 63 without decoupling from casing 62. For example, and as shown in FIGS. 8A-9B, core 66 may be shaped to define a socket 74 that has a transverse cross-sectional shape that is larger than a transverse cross-sectional shape of pin 70. Pin 70 is fixedly coupled to casing 62 and movably-coupled, via socket 74, to core 66. Due to the difference in size between the respective cross-sectional shapes of pin 70 and socket 74, core 66 is movable within cavity 63 without decoupling from casing 62.

In the unlocked configuration of device 60, lumen L3 is typically aligned between openings 64, i.e., the lumen is typically disposed on an axis between the openings. Typically, thereby, in the unlocked configuration, lumen L3 is generally in fluid communication with openings 64.

In the unlocked configuration, sutures 34a and 34b are slidable through device 60, i.e., through openings 64 and lumen L3. That is, in the unlocked configuration, the device is slidably coupled to the sutures, i.e., is slidable over the sutures. Typically, device 60 is delivered to an anatomical site (e.g., in a vicinity of a site being treated) with sutures 34a and 34b pre-threaded through the device.

Device 60 typically further comprises and/or defines one or more cutting edges, such as cutting edges 80a and 80b, described further with reference to FIGS. 9A-B.

FIGS. 9A-B show device 60 in the locking configuration thereof, i.e., after having moved into the locking configuration. FIG. 9A shows a perspective view of device 60 being used with two sutures 34*a* and 34*b*, and FIG. 9B shows a cutaway view of the same. In the locking configuration of device 60, lumen L3 is typically not aligned between openings 64, i.e., the lumen is typically not disposed on an axis between the openings. Typically, thereby, in the locking configuration, lumen L3 is generally not in fluid communication with openings 64.

In the locking configuration, sutures 34*a* and 34*b* are generally not slidable through device 60, i.e., through openings 64 and lumen L3. That is, in the locking configuration, the device is fixedly coupled to the sutures, i.e., is generally not slidable over the sutures. Typically, the device is fixedly coupled to the sutures by sandwiching at least part of the sutures between core 66 and casing 62, as shown at coupling zone 61 in FIG. 9B.

When device 60 moves into the locking configuration, the device cuts the sutures disposed therein, at a cutting zone 65. Typically, a first cutting edge 80*a* is defined by casing 62, a second cutting edge 80*b* is defined by core 66, and when sutures 34*a* and 34*b* are slid through device 60, part of each suture is disposed between the two cutting edges. When device 60 moves into the locking configuration, the two cutting edges move toward and, typically, past each other, thereby cutting the sutures.

A portion of each suture typically remains within device 60 subsequent to the fixed-coupling of the device to the sutures. For example, and as shown in FIG. 9B, coupling zone 61 may be disposed close to one end of device 60 (e.g., in a vicinity of one opening 64), and cutting zone 65 may be disposed close to another end of the device (e.g., in a vicinity of the other opening 64).

Device 60 is typically configured to be biased such that the device moves toward the locking configuration thereof. Typically, device 60 is thus configured by comprising at least one spring 72, which moves core 66 with respect to casing 62. For such applications, the device is retained in the unlocked configuration by at least one constraint, which provides a constraining force. That is, the locking configuration is an unconstrained locking configuration, and the unlocked configuration is a constrained unlocked configuration.

For example, a portion of core 66 may protrude from a lateral surface of casing 62 when the device is in the locking configuration, and the constraint may comprise a delivery sheath (not shown), which inhibits that portion of core 66 from protruding thus. So as to move device 60 into the locking configuration (e.g., so as to fixedly couple the device to the sutures, and to cut the sutures), the operating physician removes the constraining force, e.g., by removing the constraint, such as by withdrawing the sheath, such that the device automatically moves to the locking configuration.

Reference is made to FIG. 10, which is a schematic illustration showing device 60 having been used to treat prolapse in cardiac valve 4, in accordance with some applications of the invention. Typically, device 60 is used in combination with the techniques described with reference to FIGS. 3-7, mutatis mutandis. FIG. 10 shows sutures 34*a* and 34*b* having been (1) coupled to annulus 5 at sites 6 and 8, using helical anchors 40*a* and 40*b*, (2) fixedly coupled to apparatus 60 and, thereby to each other, and (3) cut using apparatus 60.

Reference is made to FIGS. 11A-14, which are schematic illustrations of a system 100 for repairing heart valve 4, and steps in the use of the system for repairing the heart valve, in accordance with some applications of the invention. System 100 comprises a support 102 and a plurality of leaflet-piercing elements 106, configured to couple the support to the heart valve by piercing the leaflets of the heart valve and coupling to the support. Typically, leaflet-piercing elements 106 are deliverable to the valve independently of support 102.

Typically, system 100 comprises a securing element 104, which comprises elements 106. Securing element 104 typically further comprises a core 108 and a plurality of arms 110. A respective inner end of each arm 110 is coupled to core 108, from which the arms extend radially. Elements 106 are coupled to respective outer ends of each arm. Typically, securing element 104 is deliverable to the valve independently of support 102.

Coupling of securing element 104 to support 102 is facilitated by leaflet-piercing elements 106. Typically, support 102 has an inner perimeter 114 that defines an opening 115, and coupling of securing element 104 to support 102 is further facilitated by at least part of core 108 of element 104 being disposed within opening 115. Typically, core 108 is shaped to define a coupling portion 109, which secures the core within the opening. For example, coupling portion 109 may comprise, or be shaped to define, a ridge 111 which inhibits the core from being decoupled from opening 115 (e.g., coupling portion 109 locks core 108 to support 102).

FIG. 11A shows support 102 and securing element 104 individually, and FIG. 11B shows the securing element coupled to the support.

Typically, support 102 comprises a braided wire mesh, which, when unconstrained, has an expanded configuration, and can be compressed into a compressed configuration. Typically, support 102 is compressed into the compressed configuration for delivery to the heart valve, is constrained in the compressed configuration by a catheter via which the support is delivered, and automatically expands upon being released from a distal end of the catheter at the heart valve. Typically, in the compressed configuration, the support is generally cylindrical in shape. In the uncompressed configuration, support 102 defines a leaflet-engaging side 118 (typically a downstream side of the support) that is typically a flat side. In the uncompressed configuration, support 102 itself is typically flat. Further typically, in the uncompressed configuration, the support defines two adjacent layers and is generally circular (i.e., disc-shaped).

Typically, securing element 104 has a delivery configuration in which arms 110 are disposed distally to core 108, and is configured to be movable to a deployed configuration following delivery to the heart valve. Typically, element 104 is configured to be constrained in the delivery configuration by a delivery sheath, and to automatically move toward the deployed configuration upon being exposed from the sheath at the heart valve.

FIGS. 11A-14 show apparatus 100, and its use in treating tricuspid valve 94 via inferior vena cava 3 of the patient. However, the scope of the invention includes the treatment of other heart valves and the use of other access routes, mutatis mutandis. Additionally, securing element 104 is shown comprising 6 arms and leaflet-piercing elements, but may comprise other pluralities of arms and leaflet-piercing elements.

Figures 12A, 12B:
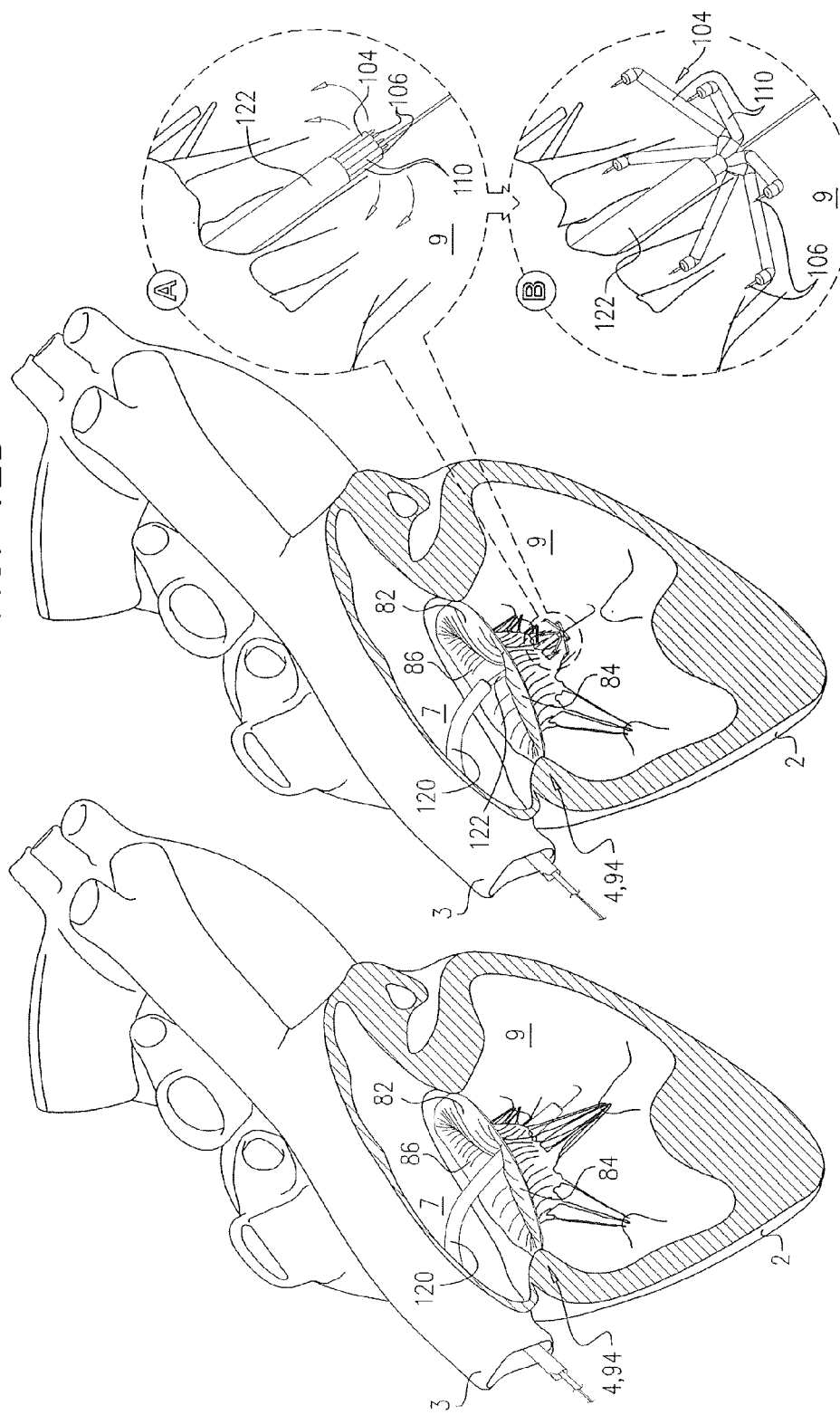

FIGS. 12A-F show steps in the use of apparatus 100 to treat (e.g., to repair) valve 4, in accordance with some applications of the invention. A catheter 120 is advanced to the valve; typically to right atrium 7 via inferior pulmonary artery 3 (e.g., transfemorally), as shown in FIG. 12A. FIG. 12B shows a delivery sheath 122 having been advanced out of a distal end of catheter 120 and, via valve 4, to a downstream side of the valve (i.e., into right ventricle 9) of the patient. FIG. 12B further shows securing element 104 having been moved (e.g., advanced distally) out of delivery sheath 122 and into ventricle 9, and expanding into the deployed configuration.

Subsequently, securing element 104 is moved (e.g., pulled) proximally, such that leaflet-piercing elements 106 pierce the leaflets of the valve, thereby coupling the securing element to the leaflets, as shown in FIG. 12C. Securing element 104 is shown comprising six arms and leaflet-piercing elements, and being coupled to the leaflets such that two leaflet-piercing elements pierce (i.e., couple to) each leaflet. It is to be noted that the scope of the present invention includes securing element 104 comprising other pluralities of arms and/or leaflet-piercing elements, and other configurations of coupling to the leaflets.

Subsequently, as shown in FIG. 12D-E, support 102 is delivered to an upstream side of the valve (i.e., into right atrium 7). Typically, support 102 is advanced through catheter 120 and, upon being exposed from the end of the catheter, automatically expands into its expanded configuration. Typically, delivery sheath 122 is typically disposed within opening 115 of the support. That is, perimeter 114 of the support is disposed around delivery sheath 122, which is typically still coupled to securing element 104. For some applications, delivery sheath 122 is coupled to securing element 104 by a lock 124 (see FIG. 13A), which is controllable from outside of the body of the patient. For some such applications, lock 124 is directly coupled to delivery sheath 122. Alternatively, lock 124 is coupled to a controller (e.g., a control wire; not shown) that is disposed within sheath 122.

Support 102 is placed against the leaflets of the valve (e.g., leaflet-engaging side 118 of the support is placed against the upstream surface of the leaflets), typically by being slid over delivery sheath 122. That is, delivery sheath 122 typically acts as a guide for support 102. FIG. 12E shows a perspective view, and FIG. 13A shows a respective cutaway view, of support 102 disposed against the leaflets. Typically, support 102 is placed, and is configured to be placed, against the leaflets of the valve such that the support overlaps more than one leaflet. That is, the support is typically placed such that respective portions of the leaflet-engaging side of the support are disposed against respective regions of respective leaflets of the valve.

FIGS. 12F and 13B show respective perspective and cutaway views of support 102 having been fixedly coupled to securing element 104, thereby sandwiching the leaflets of the valve between the support and the securing element. Leaflet-piercing elements 106 typically protrude into (e.g., through) support 102. FIGS. 12F and 13B also show catheter 120 and sheath 122 having been removed from the body of the patient. Typically, this fixed coupling is performed by securing element 104 is held immobile or pulled proximally, while support 102 is pushed distally, such that inner perimeter 114 of the support is slid over at least part of core 108 of the coupling element. For example, the support may be slid over coupling portion 109, such that ridge 111 is 'clicked' into place. Typically, support 102 is pushed distally using catheter 120 and/or a separate controller (not shown). If support 102 is pushed using catheter 120, the catheter has an outer diameter that is greater than the diameter of opening 115 of the support.

FIG. 13B shows arms 110 of securing element 104 as being bent compared to the appearance of the arms in FIG. 13A. For some applications of the invention, arms 110 are resilient, and are configured to be bent by the coupling of element 104 to support 102, acting like a spring. This configuration facilitates the coupling of apparatus 100 to the valve leaflets by transferring force from the coupling of coupling portion 109 and perimeter 114, to leaflet-piercing elements 106, thereby holding leaflet-piercing elements 106 within the leaflets and within mesh 112 of support 102. That is, coupling of coupling portion 109 of core 108 to the support facilitates coupling of the leaflet-piercing elements to the support. For some applications of the invention, leaflet-piercing elements 106 comprise straight spikes. For other applications of the invention, leaflet-piercing elements 106 comprise barbs or hooks, so as to facilitate fixed coupling of the leaflet-piercing elements directly to mesh 112.

As shown in FIGS. 12F and 13B, when apparatus 100 is implanted (i.e., coupled to the leaflets of the heart valve), arms 110 of securing element 104 are typically disposed on one side of the valve, and both coupling portion 109 and leaflet-piercing elements 106 are coupled to support 102 on the other side of the valve. Thereby, for some applications, securing element 104 is coupled to support 102 only at the upstream side of the heart valve of the patient.

FIGS. 12A-13B show securing element 104 being moved proximally (i.e., upstream), so as to couple to the valve leaflets, prior to the delivery of support 102. However, for some applications of the invention, support 102 is delivered before moving element 104 proximally.

Figure 14:
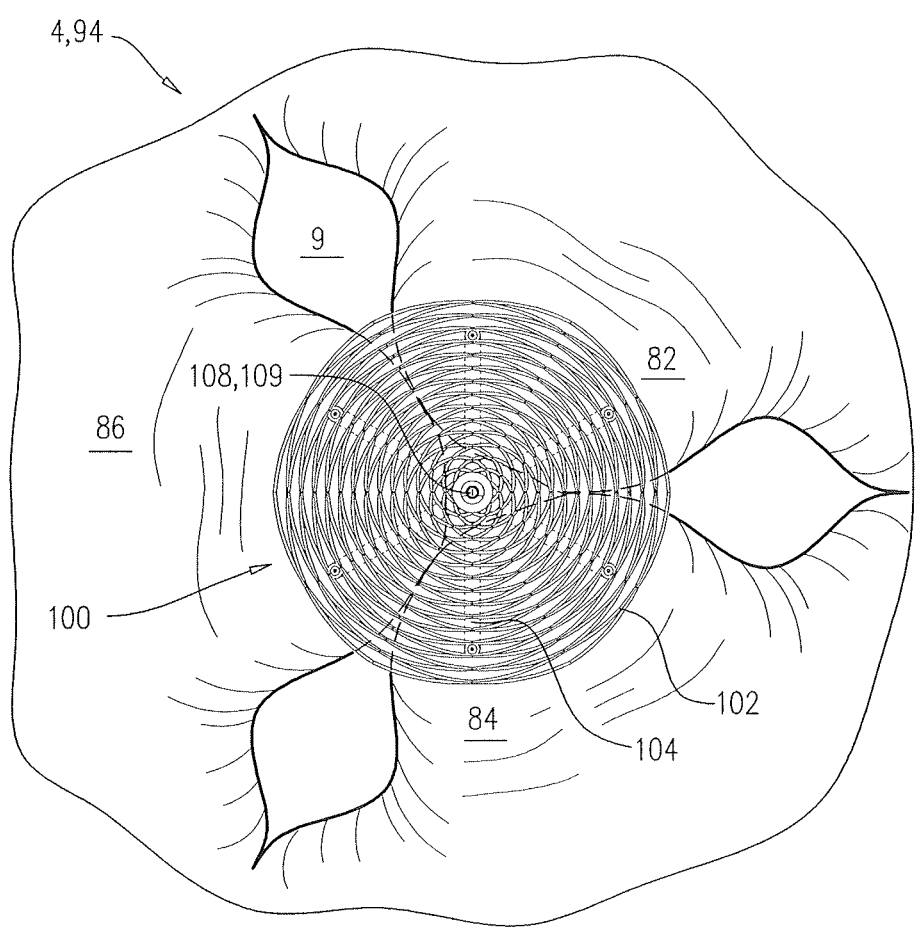

FIG. 14 is an atrial-side view of apparatus 100 having been used to repair valve 4 (e.g., tricuspid valve 94), as described in FIGS. 12A-13B. Support 102 is typically coupled to the leaflets of the valve such that the support overlaps more than one leaflet. That is, the support is typically coupled to the valve such that respective regions of the support are disposed against respective portions of respective leaflets of the valve. The cusps of the leaflets of the valve are typically held close to each other (e.g., touching each other) by apparatus 100, which is thereby disposed generally centrally in the valve. Typically, portions of the leaflets between apparatus 100 and the leaflet commissures (e.g., APC 88) are not held close to each other, and move with the beating of the heart. That is, these portions of the leaflets typically open during ventricular diastole and close during ventricular systole, thereby forming three orifices which typically act as separate valves. FIG. 14 shows these portions of the leaflets open (i.e., during diastole), such that right ventricle 9 is visible therebetween.

For some applications of the invention, support 102 is dimensioned to cover more than 10% and/or less than 90% (e.g., between 10% and 90%, such as between 10% and 30%) of the area defined by the native orifice of the heart valve. For example, a support of desired dimensions may be selected according to the valve and/or patient being treated (e.g., following measurement of the valve being treated).

It is hypothesized that the use of apparatus 100 as described with reference to FIGS. 11-14 reduces heart valve regurgitation, and may be used to repair a diseased heart valve.

Reference is now made to FIG. 15. Although apparatus 100 is shown hereinabove being configured and used, to repair tricuspid valve 94, the apparatus may be configured and used with other heart valves. For example, FIG. 15 shows apparatus 100 having been used to repair a mitral valve 130 of a patient, whereby support 102 is disposed in a right atrium 137 of the patient, and securing element 104 (not visible in FIG. 15) is disposed in a right ventricle 139 of the patient. For a bicuspid heart valve such as mitral valve 130, two orifices are typically formed between apparatus 100 and the commissures.

Apparatus 100 is typically coupled to the heart valve being treated, such that support 102 is disposed against an upstream side of the valve (i.e., an upstream side of the valve leaflets), and securing element 104 is disposed against a downstream side of the valve (i.e., against a downstream side of the valve leaflets). However, for some applications, apparatus 100 is coupled to the heart valve such that support 102 is disposed against the downstream side of the valve, and securing element 104 is disposed against the upstream side of the valve.

Apparatus 100 is typically delivered to the heart valve percutaneously (e.g., transcatheterally and/or translumically). Apparatus 100 is shown being delivered transluminally from an upstream side of the valve (e.g., via the inferior vena cava). That is, typically, from the perspective of the operating physician, the upstream side of the valve is the proximal side of the valve, and the downstream side of the valve is the distal side of the valve. However, it is to be noted that the scope of the present invention includes delivery from a downstream side of the valve (e.g., transapically, or via the aorta), mutatis mutandis.

Reference is now made to FIGS. 8A-15. Typically, device (FIGS. 8A-10) and system 100 (9A-15) are used in catheter-based procedures or minimally-invasive procedures. For some applications, device 60 (FIGS. 8A-10) and system 100 (9A-15) may be used in a surgical procedure, e.g., an open-heart procedure.

Reference is made to FIGS. 1A-15. It is to be noted that devices 22 and 60, and system 100 described herein may be used in any suitable location in the body of the patient. For example, devices 22 and 60 can be used to secure sutures in any part of the body. Additionally, it is to be noted that devices 22 and 60, and system 100 described herein may be used in any cardiac valve (i.e., the mitral, the tricuspid, the pulmonary, and the aortic valve) of the patient.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with one or more sutures, the apparatus comprising a suture-securing device, which comprises:
   a casing, which is shaped to define a first cutting edge, a cavity, and two openings in the casing at opposite ends of the casing, wherein the one or more sutures are disposable through the two openings; and
   a core, which is (a) disposed in the cavity, and (b) shaped to define a second cutting edge and a lumen, wherein the one or more sutures are disposable in the lumen,
   wherein the suture-securing device is configured:
   (i) to have an unlocked configuration in which the one or more sutures are disposable within and slidable through the two openings and the lumen, and a locking configuration in which the one or more sutures are inhibited from sliding through the two openings and the lumen,
   (ii) to be movable from the unlocked configuration to the locking configuration, such that, when the one or more sutures are disposed within the two openings and the lumen, and the suture-securing device moves from the unlocked configuration to the locking configuration, the suture-securing device (1) cuts entirely through the one or more sutures at a cutting site of the suture-securing device by pushing the one or more sutures against the first and the second cutting edges, and (2) becomes fixedly coupled to the one or more sutures at a coupling site of the suture-securing device, and
   (iii) to be suspended along the one or more sutures in the locking configuration with the opposite ends of the casing disposed entirely within a body of a patient.

2. The apparatus according to claim 1,
   wherein the two openings are provided along a longitudinal axis of the casing,
   wherein in the unlocked configuration of the suture-securing device, the lumen of the core is disposed along the axis, and between the two openings, and
   wherein in the locking configuration of the suture-securing device, the core is disposed with respect to the casing in a manner in which the lumen of the core is not disposed along the axis.

3. The apparatus according to claim 1,
   wherein the unlocked configuration comprises a constrained configuration, and the locking configuration comprises an unconstrained configuration, and
   wherein the suture-securing device is configured to be retained in the constrained unlocked configuration by a constraining force, and to automatically move toward the unconstrained locking configuration when the constraining force is removed.

4. The apparatus according to claim 3, wherein the apparatus further comprises a constraint, configured to provide the constraining force.

5. A method for use with one or more sutures at an anatomical site of a patient, the method comprising:
   delivering, to a vicinity of the anatomical site, a suture-securing device that includes (1) a casing, which is shaped to define a first cutting edge, a cavity, and two openings in the casing at opposite ends of the casing, wherein the one or more sutures are disposable through the two openings and the two openings, and (2) a core, which is (a) disposed in the cavity, and (b) shaped to define a second cutting edge and a lumen, wherein the one or more sutures are disposable in the lumen;
   sliding the suture-securing device over at least part of the one or more sutures while the suture-securing device is in an unlocked configuration in which the one or more sutures are slidable through the two openings and the lumen; and
   subsequently, by moving the suture-securing device into a locking configuration, simultaneously (1) inhibiting the one or more sutures from sliding through the lumen by fixedly coupling the suture-securing device to the one or more sutures at a coupling site of the suture-securing device, and (2) cutting entirely through the one or more sutures at a cutting site of the suture-securing device by pushing the one or more sutures against the first and the second cutting edges, such that the suture-securing device is suspended along the one or more sutures in the locking configuration with the opposite ends of the casing disposed entirely within a body of the patient.

6. The method according to claim 5, wherein the suture-securing device is configured to be constrained in the unlocked configuration by a constraining force, and wherein moving the suture-securing device into the locking configuration comprises removing the constraining force.

* * * * *